United States Patent
Nelson et al.

(10) Patent No.: US 6,348,604 B1
(45) Date of Patent: Feb. 19, 2002

(54) PHOTOCHROMIC NAPHTHOPYRANS

(75) Inventors: Clara M. Nelson; Anu Chopra, both of Pittsburgh; David B. Knowles, Apollo; Barry Van Gemert, Murrysville; Anil Kumar, Pittsburgh, all of PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 09/656,509

(22) Filed: Sep. 6, 2000

Related U.S. Application Data

(60) Provisional application No. 60/154,429, filed on Sep. 17, 1999, and provisional application No. 60/164,652, filed on Nov. 10, 1999.

(51) Int. Cl.[7] .......................... G02B 5/23; C07D 311/92
(52) U.S. Cl. ...................... 549/389; 544/150; 546/196; 252/586
(58) Field of Search .................... 544/150; 546/196; 549/389; 252/586

(56) References Cited

U.S. PATENT DOCUMENTS

| | | |
|---|---|---|
| 3,361,706 A | 1/1968 | Meriwether et al. |
| 3,562,172 A | 2/1971 | Ono et al. |
| 3,567,605 A | 3/1971 | Becker |
| 3,578,602 A | 5/1971 | Ono et al. |
| 3,627,690 A | 12/1971 | Casella et al. |
| 3,971,872 A | 7/1976 | LeBeouf |
| 4,215,010 A | 7/1980 | Hovey et al. |
| 4,342,668 A | 8/1982 | Hovey |
| 4,719,296 A | 1/1988 | Irie et al. |
| 4,816,584 A | 3/1989 | Kwak et al. |
| 4,818,096 A | 4/1989 | Heller et al. |
| 4,826,977 A | 5/1989 | Heller et al. |
| 4,873,029 A | 10/1989 | Blum |
| 4,880,667 A | 11/1989 | Welch |
| 4,931,219 A | 6/1990 | Kwiatkowski et al. |
| 4,931,220 A | 6/1990 | Haynes et al. |
| 5,066,818 A | 11/1991 | Van Gemert et al. |
| 5,166,345 A | 11/1992 | Akashi et al. |
| 5,200,116 A | 4/1993 | Heller |
| 5,236,958 A | 8/1993 | Miyashita |
| 5,238,981 A | 8/1993 | Knowles |
| 5,252,742 A | 10/1993 | Miyashita |
| 5,274,132 A | 12/1993 | Van Gemert |
| 5,359,085 A | 10/1994 | Iwamoto et al. |
| 5,384,077 A | 1/1995 | Knowles |
| 5,405,958 A | 4/1995 | Van Gemert |
| 5,429,774 A | 7/1995 | Kumar |
| 5,458,814 A | 10/1995 | Kumar et al. |
| 5,466,398 A | 11/1995 | Van Gemert et al. |
| 5,488,119 A | 1/1996 | Fischer-Reimann et al. |
| 5,514,817 A | 5/1996 | Knowles |

(List continued on next page.)

FOREIGN PATENT DOCUMENTS

| | | |
|---|---|---|
| EP | 0926146 A1 | 6/1999 |
| JP | 6-306354 A | 11/1994 |
| JP | 8-295690 A | 11/1996 |
| WO | WO 98/04937 | 2/1998 |
| WO | WO 98/42693 | 10/1998 |
| WO | WO 98/42695 | 10/1998 |
| WO | WO 98/57943 | 12/1998 |
| WO | WO 99/15518 | 4/1999 |
| WO | WO 99/31081 | 6/1999 |
| WO | WO 00/18755 | 4/2000 |
| WO | WO 00/35902 | 6/2000 |

OTHER PUBLICATIONS

Van Gemert and Kish, PPG Technology Journal, vol. 5, "The Intricacies of Color Matching Organic Photochromic Dyes", p 53–61, 1999.

Friedel–Crafts and Related Reactions, George Olah, Interscience Publishers, 1964, vol. 3, Chapter XXXI (Aromatic Ketone Synthesis).

*Primary Examiner*—Robert W. Ramsuer
*Assistant Examiner*—Andrea M. D'Souza
(74) *Attorney, Agent, or Firm*—Frank P. Mallak

(57) ABSTRACT

Described are novel photochromic 2H-naphtho[1,2-b]pyran compounds essentially characterized by having two adjacent moderate to strong electron donor substituents at the 8 and 9 positions or a fused heterocyclic group formed by the substituents coming together, weak to moderate electron donors at the 2 position and a rating of at least 80 in the Relative ΔOD at Saturation Test. The compounds also have certain substituents at the 5 position and optionally at the 6 position of the naphtho portion of the compound. These compounds may be represented by the following graphic formula:

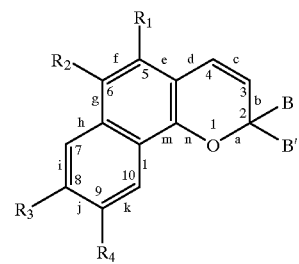

Also described are polymeric organic host materials that contain or that are coated with such compounds. Optically clear articles such as ophthalmic lenses or adjacent plastic transparencies that incorporate the novel naphthopyran compounds or combinations thereof with complementary photochromic compounds, e.g., certain other naphthopyrans, benzopyrans, and spiro(indoline)type compounds, are also described.

23 Claims, No Drawings

U.S. PATENT DOCUMENTS

| | | |
|---|---|---|
| 5,552,090 A | 9/1996 | Van Gemert et al. |
| 5,552,091 A | 9/1996 | Kumar |
| 5,565,147 A | 10/1996 | Knowles et al. |
| 5,573,712 A | 11/1996 | Kumar et al. |
| 5,578,252 A | 11/1996 | Van Gemert et al. |
| 5,637,262 A | 6/1997 | Van Gemert et al. |
| 5,645,767 A | 7/1997 | Van Gemert |
| 5,651,923 A | 7/1997 | Kumar et al. |
| 5,656,206 A | 8/1997 | Knowles et al. |
| 5,658,500 A | 8/1997 | Kumar et al. |
| 5,658,501 A | 8/1997 | Kumar et al. |
| 5,674,432 A | 10/1997 | Knowles et al. |
| 5,698,141 A | 12/1997 | Kumar |
| 5,753,146 A | 5/1998 | Van Gemert et al. |
| 5,936,016 A | 8/1999 | Lareginie et al. |
| 5,961,892 A | 10/1999 | Van Gemert et al. |
| 5,965,630 A | 10/1999 | Imafuku et al. |
| 5,965,631 A | 10/1999 | Nicholson et al. |
| 6,113,814 A | 9/2000 | Van Gemert et al. |

PHOTOCHROMIC NAPHTHOPYRANS

CROSS REFERENCE TO RELATED APPLICATIONS

This application claims the benefit of U.S. provisional application Serial Nos. 60/154,429 filed Sep. 17, 1999 and 60/164,652 filed Nov. 10, 1999.

DESCRIPTION OF THE INVENTION

The present invention relates to certain novel naphthopyran compounds. More particularly, this invention relates to novel photochromic naphthopyran compounds and to compositions and articles containing such novel naphthopyran compounds. When exposed to light radiation containing ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

U.S. Pat. No. 5,066,818 describes various 3,3-diaryl-3H-naphtho[2,1-b]pyrans as having desirable photochromic properties, i.e., high colorability and acceptable fade, for ophthalmic and other applications. Also disclosed by way of comparative example in the '818 patent are the isomeric 2,2-diaryl-2H-naphtho[1,2-b]pyrans, which are reported to require unacceptably long periods of time to fade after activation.

U.S. Pat. No. 3,627,690 describes photochromic 2,2-disubstituted-2H-naphtho[1,2-b]pyran compositions containing minor amounts of either a base or weak-to-moderate strength acid. The addition of either an acid or base to the naphthopyran composition is reported to increase the fade rate of the colored naphthopyrans, thereby making them useful in eye protection applications such as sunglasses. It is reported therein further that the fade rate of 2H-naphtho[1,2-b]pyrans without the aforementioned additives ranges from several hours to many days to reach complete reversion. U.S. Pat. No. 5,458,814 discloses 2H-naphtho[1,2-b]pyrans substituted in the 5- and 6-positions that possess a reasonable rate of fade as well as high colorability. The compounds exhibit activated colors ranging from yellow to red/purple.

While the activated form of a typical organic photochromic molecule absorbs in the visible region over a relatively narrow range (Van Gemert and Kish, PPG Technology Journal, Vol. 5, pg. 53–61, 1999), naphthopyrans having two absorption bands, are known. U.S. Pat. No. 5,645,767 discloses photochromic indeno[2,1-f]naphtho[1,2-b]pyrans having a blue/gray activated color. A blue/gray color will be perceived when there is a major absorption of visible light in the 580–620 nm range coupled with a minor absorption in the 420–500 nm range.

International Patent Application Publication No. WO 99/15518 discloses photochromic indeno[2,1-f]naphtho[1,2-b]pyrans having a green activated color. A greenish color will be perceived when there is a major absorption of visible light in the 580–620 nm range coupled with a major absorption of roughly equal intensity in the 400–480 nm range.

International Patent Application Publication No. WO 98/42693 describes naphtho[1,2-b]pyrans having amino functional groups as substituents at the 7- or 9-positions of the naphthopyran ring. These compounds are disclosed as exhibiting a brown or red/brown activated color. A red/brown color will be perceived when there is a major absorption of visible light in the 420–500 nm range coupled with a minor absorption in the 520–560 nm range.

International Patent Application Publication No. WO 98/04937 describes naphtho[1,2-b]pyrans having alkoxy groups as substituents at the 7- and 9-positions of the naphthopyran ring. The activated forms of these compounds exhibit two intense absorption bands in the visible light range. It is reported that the optical density of the band absorbing at lower wavelengths (band "A") in some cases is higher than the optical density of the band absorbing at higher wavelengths (band "B"), but in the majority of cases the band "A" is of lower optical density than band "B".

International Patent Application Publication No. WO 00/35902 describes 2H-naphtho[1,2-b]pyrans having various substituents. It is disclosed that when a substituent is present at the 5 carbon atom of a 2,2-diaryl-2H-naphtho[1,2-b]pyran, the intensity of the color generated can be enhanced by placing an electron-releasing group at the 8 carbon atom. This effect may be further augmented by placing additional electron-releasing groups at carbon atoms 7 and/or 10. It is further disclosed that the intensity of the generated color can be diminished by placing electron-releasing substituents at carbon atoms 9 or 7. There is no mention in this application of the naphthopyrans having multiple absorption bands nor the relative intensities of such bands.

While it is obvious from the previous description that it is possible to obtain many complex activated colors, it is not disclosed in any of these patents or applications how to select substituents for both the pyrano and the naphtho portions of the naphtho[1,2-b]pyran in order to control the wavelength and/or intensity of the absorbance bands within the activated visible spectra.

The present invention discloses what types of substituents and where they may be placed in order to control the wavelength and/or intensity of the visible absorbance bands of 2H-naphtho[1,2-b]pyrans having 2 intense spectral bands in the visible spectrum. Such 2H-naphtho[l,2-b]pyrans are essentially characterized by either two adjacent moderate to strong electron donor substituents at the 8 and 9 positions or a fused heterocyclic group formed by the substituents at the 8 and 9 positions coming together and at the 2 position, weak to moderate electron donor substituent(s). The compounds of the present invention also have a substituent at the 5 position and an optional substituent at the 6 position. The selection and placement of these substituents being done so that the photochromic naphthopyrans demonstrate a rating of at least 80 in the Relative ΔOD at Saturation Test, described hereinafter.

Clearly with this understanding, not only can compounds exhibiting colors including an apparent blended brown, gray or a green activated color be obtained, but one skilled in the art can now fine tune the activated visible spectrum to meet specific needs. For example, the use of certain individual compounds of the present invention may eliminate the need for combining two or more compounds to obtain a preferred shade or version of the neutral colors such as gray or brown. In addition, these compounds have demonstrated a high molar absorptivity (or molar extinction coefficient) in the ultraviolet (UV) light range, an acceptable fade rate without the addition of acids or bases, a high activated intensity, and a high coloration rate. These compounds are also reported to be more resistant to fatigue than other compounds having equal absorbance in the 400 to 500 nanometer range.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

In accordance with the present invention, it has now been discovered that certain novel 2H-naphtho[1,2-b]pyrans having an "A" band in the 420–500 nm region and a "B" band in the 480–620 nm region of the activated visible spectrum and having a rating of 80 or higher in the Relative ΔOD at Saturation Test may be prepared. The Relative ΔOD at Saturation Test is described in Example 9. The ratings of the test are defined herein as the result obtained when the optical density of band "A" is divided by the optical density of band "B" and multiplied by 100. It is believed that compounds having a rating of 80 or higher are most valuable for formulating neutral grays, greens and browns for commercial photochromic ophthalmic eyewear.

The naphthopyrans of the present invention may have a rating in the Relative ΔOD at Saturation Test of at least 80, preferably at least 90, more preferably at least 100 and most preferably, at least 130. The rating is expected to be less than 1000, preferably less than 800, more preferably less than 500 and most preferably less than 300. The rating for the naphthopyrans may range between any combination of these values, inclusive of the recited values, e.g., from at least 80 to less than 1000. The naphthopyrans of the present invention may have a rating greater than 1000 if the two absorption bands are distinguishable and an optical density is obtainable for the calculation.

Preparation of such compounds is achieved by balancing the effects of the potential substituents as described hereinafter. For example, the "A" band of these compounds can be enhanced relative to the "B" band by employing strong electron donor substituents in the 8-position, moderate electron donors in the 9-position, and weak to moderate electron donors in the 2-position of the pyran ring. Compounds having relatively equivalent intensity for the "A" and "B" bands can be obtained by having electron donors of relatively equal intensity at the 8- and 9-positions and weak to moderate electron donors at the 2-position of the pyran ring. Strong electron donors on an aryl grouping at the 2-position of the pyran will enhance the "B" band relative to the "A" band. The intensity or strength of the electron donors at the 2-position of the pyran ring will not only effect the relative intensity of the two spectral bands, but also their position. For example, strong electron donors on an aryl grouping at the 2-position will shift both bands bathochromically (the "B" band more than the "A" band).

The relative strength of electron donor groups is frequently described by Hammett Sigma values (specifically $\sigma_p$ values). A tabular listing of $\sigma_p$ constants for a variety of substituents can be found in "Exploring QSAR, Hydrophobic, Electronic, and Steric Constants, C. Hansch, A. Leo, and D. Hoekman, Eds., Published by The American Chemical Society, Washington, D.C., 1995, which disclosure is incorporated herein by reference. Examples of strong electron donors, defined herein as having a Hammett $\sigma_p$ value of between –1.0 and –0.5, that may be used at the 8- and 9-positions or at the para position of an aryl grouping present at the 2-position of the pyrano portion of the naphthopyran include amino, monoalkylamino, dialkylamino, morpholino, and piperidino. Examples of moderate electron donors, defined herein as having a $\sigma_p$ value of between –0.49 and –0.20 that may be used at the 8- and 9-positions or at the para position of an aryl grouping present at the 2-position of the pyrano portion of the naphthopyran include ethoxy, methoxy, and p-aminophenyl. Examples of weak electron donors, defined herein as having a Hammett $\sigma_p$ value of between –0.01 and –0.19 that may be used at the 2-position of the pyrano portion of the naphthopyran include methyl, ethyl, phenyl, naphthyl, and tolyl.

The compounds of the present invention may be described as photochromic compounds of 2H-naphtho[1,2-b]pyran structure, essentially characterized by having moderate to strong electron donor groups $R_3$ and $R_4$ at the 8 and 9 positions, respectively, or a heterocyclic ring fused to the j side of the naphtho portion of the compound and at the 2 position, weak to moderate electron donor substituents. Also present are substituents at the 5 position and optionally, at the 6 position of the naphtho portion of the compound. These compounds may be represented by the following graphic formula I in which the letters a through n on the outside of the ring structure represent the sides of the naphthopyran ring, and the numbers on the inside of the ring structure represent the numbers of the ring carbon atoms or ring positions of the naphthopyran:

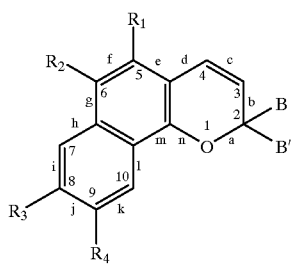

I

In graphic formula I, the substituent $R_4$ is the following group (i) and $R_3$ is selected from the group consisting of (i), (ii), (iii) and (iv):

(i) the group, $-OR_{12}$, wherein $R_{12}$ is hydrogen, $C_1$–$C_6$ alkyl, the unsubstituted, mono- and disubstituted aryl groups, phenyl and naphthyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl, $C_3$–$C_7$ cycloalkyl, mono ($C_1$–$C_4$)alkyl substituted $C_3$–$C_7$ cycloalkyl, $C_1$–$C_6$ chloroalkyl, $C_1$–$C_6$ fluoroalkyl, allyl or $R_{12}$ is the group $-CH(R_{13})Q$, wherein $R_{13}$ is hydrogen or $C_1$–$C_3$ alkyl and Q is $-CN$, $-CF_3$ or $-COOR_7$ ($R_7$ being the same as defined hereinafter), each of said phenyl and naphthyl group substituents being $C_1$–$C_6$ alkyl or $C_1$–$C_6$ alkoxy;

(ii) the group, $-N(R_{14})R_{15}$, wherein $R_{14}$ and $R_{15}$ are each selected from the group consisting of hydrogen, $C_1$–$C_8$ alkyl, phenyl, naphthyl, the heteroaromatic groups furanyl, benzofuran-2-yl, benzofuran-3-yl, thienyl, benzothien-2-yl, benzothien-3-yl, dibenzofuranyl, dibenzothienyl, benzopyridyl and fluorenyl, a $C_1$–$C_8$ alkylaryl group, $C_3$–$C_{20}$ cycloalkyl, $C_4$–$C_{20}$ bicycloalkyl, $C_5$–$C_{20}$ tricycloalkyl and $C_1$–$C_{20}$ alkoxyalkyl, wherein said aryl group is phenyl or naphthyl;

(iii) a nitrogen containing ring represented by the following graphic formula:

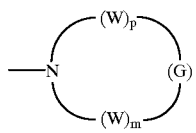

IIA wherein W is selected from the group consisting of $-CH_2-$, $-CH(R_{16})-$, $-C(R_{16})(R_{16})-$, $-CH$ (aryl)$-$, $-C(aryl)_2-$, $-C(R_{16})(aryl)-$, and G is selected from the group consisting of $-W-$, $-O-$, $-S-$, $-S(O)-$, $-S(O_2)-$, $-NH-$, $-NR_{16}-$ and $-N$-aryl, wherein $R_{16}$ is $C_1$–$C_6$ alkyl, aryl is phenyl or naphthyl, m is the integer 1, 2 or 3, and p is the integer 0, 1, 2 or 3 and when p is O, G is W; and (iv) a group represented by the following graphic formulae:

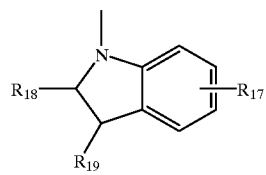

IIB

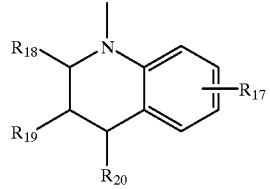

IIC wherein $R_{18}$, $R_{19}$ and $R_{20}$ are each hydrogen, $C_1$–$C_5$ alkyl, phenyl or naphthyl, or the groups $R_{18}$ and $R_{19}$ may come together to form a saturated or unsaturated ring of 5 to 8 carbon atoms including the ring carbon atoms. For example, when $R_{18}$ and $R_{19}$ come together to form a ring of 6 carbon atoms on the group represented by graphic formula IIB, the resulting unsaturated group is carbazol-9-yl and the saturated group is tetrahydrocarbazol-9-yl. $R_{17}$ is $C_1$–$C_6$ alkyl, $C_1$–$C_6$ alkoxy, fluoro or chloro.

Alternatively, $R_3$ and $R_4$ together form the following graphic formula:

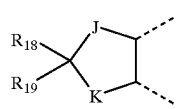

IID

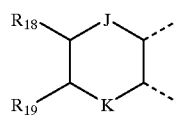

IIE wherein J and K are each oxygen or the group $-NR_{14}-$; $R_{14}$, $R_{18}$ and $R_{19}$ being the same as defined hereinbefore.

Preferably, $R_4$ is the following group (i); and $R_3$ is selected from the group consisting of:

(i) the group $-OR_{12}$, wherein $R_{12}$ is hydrogen, $C_1$–$C_4$ alkyl, an unsubstituted, mono- or di-substituted phenyl, phenyl($C_1$–$C_2$)alkyl, mono($C_1$–$C_4$)alkyl substituted phenyl($C_1$–$C_2$)alkyl, mono($C_1$–$C_4$)alkoxy substituted phenyl($C_1$–$C_2$)alkyl, $C_1$–$C_4$ alkoxy($C_2$–$C_3$)alkyl, $C_3$–$C_5$ cycloalkyl, mono($C_1$–$C_4$)alkyl substituted $C_3$–$C_5$ cycloalkyl, $C_1$–$C_4$ chloroalkyl, $C_1$–$C_4$ fluoroalkyl, allyl, each of said phenyl substituents being $C_1$–$C_3$ alkyl or $C_1$–$C_3$ alkoxy;

(ii) the group, $-N(R_{14})R_{15}$, wherein $R_{14}$ and $R_{15}$ are each selected from the group consisting of hydrogen, $C_1$–$C_4$ alkyl, phenyl, $C_1$–$C_6$ alkylphenyl, $C_3$–$C_{10}$ cycloalkyl, and $C_1$–$C_{10}$ alkoxyalkyl; and (iii) a nitrogen containing ring represented by graphic formula IIA wherein W is selected from the group consisting of $-CH_2-$, $-CH(R_{16})-$, $-C(R_{16})$ $(R_{16})-$, $-CH$(aryl)$-$, $-C(aryl)_2-$, $-C(R_{16})$ (aryl)$-$, and G is selected from the group consisting of $-W-$, $-O-$, $-NH-$, $-NR_{16}-$ and $-N$-aryl, wherein $R_{16}$ is $C_1$–$C_4$ alkyl and aryl is phenyl or naphthyl, m is the integer 1, 2 or 3, and p is the integer 0, 1, 2 or 3 and when p is O, G is W.

Alternatively, $R_3$ and $R_4$ together form graphic formula IIE wherein J and K are each oxygen or the group —$NR_{14}$—; $R_{14}$, $R_{18}$ and $R_{19}$ being the same as defined herein before.

More preferably, $R_4$ is the following group (i); and $R_3$ is selected from the group consisting of:

(i) the group, —$OR_{12}$, wherein $R_{12}$ is hydrogen or $C_1$–$C_3$ alkyl;

(ii) the group, —$N(R_{14})R_{15}$, wherein $R_{14}$ and $R_{15}$ are each hydrogen or $C_1$–$C_3$ alkyl; and (iii) a nitrogen containing ring represented by graphic formula IIA wherein W is —$CH_2$— and G is selected from the group consisting of —W— and —O—, m is the integer 1 or 2, p is the integer 0, 1 or 2, and when p is O, G is W.

Alternatively, $R_3$ and $R_4$ together form the compound represented by graphic formula IIE wherein J and K are each oxygen.

In graphic formulae I, $R_1$ may be the group T; $R_2$ may be the group T or a mono-T-substituted phenyl. The T group may be represented by the general formula:

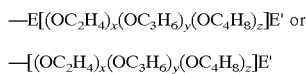

wherein —E is —C(O)— or —$CH_2$—, and E' is $C_1$–$C_3$ alkoxy or a polymerizable group, i.e., any functional group capable of participating in a polymerization reaction. Polymer forming methods in which the compounds of the present invention may participate include radical polymerization, and such other polymerization processes as are described in *Ullmann's Encyclopedia of Industrial Chemistry*, "Polymerization Processes", Vol. 21A, pp 305 to 428, which disclosure is incorporated herein by reference. The polymerizable groups may be selected from the group consisting of hydroxy, (meth)acryloxy, and epoxy, e.g., oxiranylmethyl. When there are 2 or more polymerizable groups on the naphthopyran, they may be the same or different The group, —$(OC_2H_4)_x$—, represents poly(ethylene oxide); —$(OC_3H_6)_y$—, represents poly(propylene oxide); and, —$(OC_4H_8)_z$—, represents poly(butylene oxide). When used in combination, the poly(ethylene oxide), poly (propylene oxide) and poly(butylene oxide) groups of T may be in a random or block order within the T moiety. The letters x, y and z are each a number between 0 and 50 and the sum of x, y and z is between 2 and 50. The sum of x, y and z may be any number that falls within the range of 2 to 50, e.g., 2, 3 . . . 50. The sum may also range from any lower number to any higher number within the range of 2 to 50, e.g., 6 to 50, 31 to 50. The numbers for x, y, and z are average values and can be partial numbers, e.g., 9.5.

Alternatively, the substituents $R_1$ or $R_2$ in graphic formula I may be a group other than T or mono-T-substituted phenyl. $R_1$ may be selected from —$CH_2X$, —$C(V)_2X$ or —$C(O)Y$, wherein: X is hydrogen, $C_1$–$C_6$ alkyl, chloro, fluoro, bromo, hydroxy, benzoyloxy, $C_1$–$C_6$ alkoxy, $C_2$–$C_6$ acyloxy, amino, mono($C_1$–$C_6$)alkylamino, di($C_1$–$C_6$) alkylamino, morpholino, piperidino, 1-indolinyl, pyrrolidyl, trimethylsilyloxy or the group, —$OCH(R_7)Z$; V is $C_1$–$C_6$ alkyl or the unsubstituted, mono- or di-substituted aryl groups, phenyl or naphthyl, said aryl group substituents being $C_1$–$C_6$ alkyl or $C_1$–$C_6$ alkoxy; Y is hydrogen, hydroxy, $C_1$–$C_6$ alkyl, the unsubstituted, mono- or di-substituted aryl groups phenyl or naphthyl, the group, —$OCH(R_7)Z$, —$OR_8$, or —$N(R_9)(R_{10})$ or an unsubstituted, mono-substituted or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl, each of said phenyl, naphthyl and heterocyclic ring substituents being $C_1$–$C_6$ alkyl or $C_1$–$C_6$ alkoxy; Z is —CN, —$CF_3$, chloro, fluoro, or —$C(O)R_{11}$; $R_7$ is hydrogen or $C_1$–$C_6$ alkyl; $R_{11}$ is hydrogen, $C_1$–$C_6$ alkyl or $C_1$–$C_6$ alkoxy; $R_8$ is hydrogen, $C_1$–$C_6$ alkyl, allyl, phenyl ($C_1$–$C_3$)alkyl, mono($C_1$–$C_6$)alkyl substituted phenyl ($C_1$–$C_3$)alkyl, mono($C_1$–$C_6$)alkoxy substituted phenyl ($C_1$–$C_3$)alkyl, ($C_1$–$C_6$)alkoxy($C_2$–$C_4$)alkyl, $C_1$–$C_6$ haloalkyl, or the unsubstituted, mono- or di-substituted aryl groups, phenyl or naphthyl, each of said phenyl and naphthyl group substituents being $C_1$–$C_6$ alkyl or $C_1$–$C_6$ alkoxy, said halo substituents being chloro or fluoro; and $R_9$ and $R_{10}$ are each selected from the group consisting of hydrogen, $C_1$–$C_6$ alkyl, $C_5$–$C_7$ cycloalkyl, phenyl, mono-substituted phenyl and di-substituted phenyl, said phenyl substituents being $C_1$–$C_6$ alkyl or $C_1$–$C_6$ alkoxy.

Preferably, $R_1$ is selected from —$CH_2X$, —$C(V)_2X$ or —$C(O)Y$, wherein: X is hydrogen, $C_1$–$C_4$ alkyl, hydroxy, benzoyloxy, $C_1$–$C_4$ alkoxy, $C_2$–$C_4$ acyloxy, amino, mono ($C_1$–$C_4$)alkylamino, di($C_1$–$C_4$)alkylamino, morpholino, piperidino, 1-indolinyl, pyrrolidyl; V is $C_1$–$C_4$ alkyl or the unsubstituted, mono- or di-substituted aryl groups, phenyl or naphthyl, said aryl group substituents being $C_1$–$C_4$ alkyl or $C_{1-4}$ alkoxy; Y is hydrogen, hydroxy, $C_1$–$C_4$ alkyl, an unsubstituted, mono- or di-substituted phenyl, the group, —$OCH(R_7)Z$, —$OR_8$, or —$N(R_9)(R_{10})$ or an unsubstituted or mono-substituted heterocyclic ring selected from the group consisting of 1-indolinyl, morpholino, piperidino, and 1-pyrrolidyl, each of said phenyl and heterocyclic ring substituents being $C_1$–$C_4$ alkyl or $C_1$–$C_4$ alkoxy; Z is —CN or —$C(O)R_{11}$; $R_7$ is hydrogen or $C_1$–$C_4$ alkyl; $R_{11}$ is $C_1$–$C_4$ alkyl or $C_1$–$C_4$ alkoxy; $R_8$ is hydrogen, $C_1$–$C_4$ alkyl, phenyl ($C_1$–$C_2$)alkyl, mono($C_1$–$C_4$)alkyl substituted phenyl ($C_1$–$C_2$)alkyl, mono($C_1$–$C_4$)alkoxy substituted phenyl ($C_1$–$C_2$)alkyl, mono($C_1$–$C_4$)alkoxy($C_2$–$C_3$)alkyl, or an unsubstituted, mono- or di-substituted phenyl, each of said phenyl substituents being $C_1$–$C_4$ alkyl or $C_1$–$C_4$ alkoxy, and $R_9$ and $R_{10}$ are each selected from the group consisting of hydrogen, $C_1$–$C_4$ alkyl, $C_5$–$C_6$ cycloalkyl, phenyl, mono-substituted phenyl and di-substituted phenyl, said phenyl substituents being $C_1$–$C_4$ alkyl or $C_1$–$C_4$ alkoxy.

More preferably, $R_1$ is selected from —$CH_2X$, —$C(V)_2X$ or —$C(O)Y$, wherein: X is hydrogen, $C_1$–$C_3$ alkyl, hydroxy, benzoyloxy, $C_1$–$C_3$ alkoxy, $C_2$–$C_3$ acyloxy, amino, mono ($C_1$–$C_3$)alkylamino, di($C_1$–$C_3$)alkylamino, morpholino or piperidino; V is $C_1$–$C_3$ alkyl or an unsubstituted or mono-substituted phenyl, said phenyl group substituents being $C_1$–$C_3$ alkyl or $C_1$–$C_3$ alkoxy; Y is hydrogen, hydroxy, $C_1$–$C_3$ alkyl, an unsubstituted or mono-substituted phenyl, the group, —$OR_8$, or —$N(R_9)(R_{10})$ or an unsubstituted or mono-substituted heterocyclic ring selected from the group consisting of 1-indolinyl, morpholino and piperidino, each of said phenyl and heterocyclic ring substituents being $C_1$–$C_3$ alkyl or $C_1$–$C_3$ alkoxy; $R_8$ is hydrogen or $C_1$–$C_3$ alkyl; and $R_9$ and $R_{10}$ are each selected from the group consisting of hydrogen, $C_1$–$C_3$ alkyl, phenyl and monosubstituted phenyl, said phenyl substituent being $C_1$–$C_3$ alkyl or $C_1$–$C_3$ alkoxy.

$R_2$ in graphic formula I may be selected from hydrogen, $C_1$–$C_6$ alkyl, $C_1$–$C_6$ alkoxy, the unsubstituted, mono- or di-substituted aryl groups, phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di-($C_1$–$C_6$)alkyl substituted diphenylamino, mono- or di-($C_1$–$C_6$)alkoxy substituted diphenylamino, morpholino, piperidino, dicyclohexylamino or pyrrolidyl, said aryl substituents being selected from the group consisting of $C_1$–$C_6$ alkyl, $C_1$–$C_6$ alkoxy, $C_3$–$C_6$ cycloalkyl, benzyl, amino, mono($C_1$–$C_6$)alkylamino, di($C_1$–$C_6$)alkylamino, dicyclohexylamino, diphenylamino, piperidino, morpholino, pyrrolidyl, pyridyl, bromo, chloro, fluoro, phenyl and naphthyl.

Preferably, $R_2$ is selected from hydrogen, $C_1$–$C_4$ alkyl, $C_1$–$C_4$ alkoxy, the unsubstituted, mono- or di-substituted aryl groups, phenyl or naphthyl, amino, mono($C_1$–$C_4$)alkylamino, di($C_1$–$C_4$)alkylamino, morpholino, piperidino, or pyrrolidyl, said aryl substituents being selected from the group consisting of $C_1$–$C_4$ alkyl, $C_1$–$C_4$ alkoxy, $C_3$–$C_5$ cycloalkyl, benzyl, amino, mono($C_1$–$C_4$)alkylamino, di($C_1$–$C_4$)alkylamino, piperidino, morpholino, chloro, fluoro and phenyl. More preferably, $R_2$ is hydrogen, $C_1$–$C_3$ alkoxy, $C_1$–$C_3$ alkyl or unsubstituted, mono- or di-substituted phenyl, said phenyl substituents being $C_1$–$C_3$ alkyl, $C_1$–$C_3$ alkoxy, chloro or fluoro.

B and B' in graphic formula I may each be selected from the group consisting of:

(i) mono-T-substituted phenyl;
(ii) the unsubstituted, mono-, di-, and tri-substituted aryl groups, phenyl and naphthyl;
(iii) 9-julolidinyl and the unsubstituted, mono- and di-substituted aromatic heterocyclic groups pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, each of said aryl and aromatic heterocyclic substituents in parts (ii) and (iii) being selected from the group consisting of hydroxy, aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di-($C_1$–$C_6$)alkylaryl($C_1$–$C_6$)alkyl, mono- and di-($C_1$–$C_6$)alkoxyaryl($C_1$–$C_6$)alkyl, mono- and di-($C_1$–$C_6$)alkylaryl($C_1$–$C_6$)alkoxy, mono- and di-($C_1$–$C_6$)alkoxyaryl($C_1$–$C_6$)alkoxy, amino, mono($C_1$–$C_6$)alkylamino, di($C_1$–$C_6$)alkylamino, diarylamino, piperazino, N-($C_1$–$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro, each aryl group described for said aryl or heteroaromatic substituent being phenyl or naphthyl;
(iv) the unsubstituted or mono-substituted groups, pyrazolyl, imidazolyl, pyridyl, pyrazolinyl, imidazolinyl, pyrrolinyl, phenothiazinyl, phenoxazinyl, phenazinyl or acridinyl, each of said substituents for said groups in (iv) being selected from the group consisting of $C_1$–$C_6$ alkyl, $C_1$–$C_4$ alkoxy, phenyl, fluoro, chloro and bromo;
(v) monosubstituted phenyl, having a substituent at the para position that is a linking group, —($CH_2$)$_t$— or —O—($CH_2$)$_t$—, wherein t is the integer 1, 2, 3, 4, 5 or 6, connected to an aryl group, e.g. phenyl or naphthyl, which is a member of another photochromic naphthopyran, such as naphtho[2,1-b]pyran or naphtho[1,2-b]pyran;
(vi) the groups represented by the following graphic formulae:

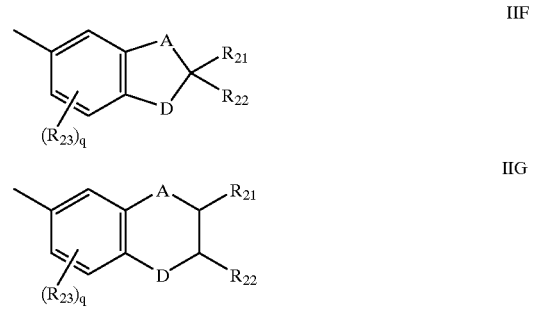

wherein A is methylene or oxygen and D is oxygen or substituted nitrogen, provided that when D is substituted nitrogen, A is methylene, said nitrogen substituents being selected from the group consisting of hydrogen, $C_1$–$C_6$ alkyl, and $C_2$–$C_6$ acyl; each $R_{23}$ is $C_1$–$C_6$ alkyl, $C_1$–$C_6$ alkoxy, hydroxy, chloro or fluoro; $R_{21}$ and $R_{22}$ are each hydrogen or $C_1$–$C_6$ alkyl; and q is the integer 0, 1, or 2;
(vii) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$)alkoxy($C_3$–$C_6$)cycloalkyl, mono($C_1$–$C_6$)alkyl($C_3$–$C_6$)cycloalkyl, chloro($C_3$–$C_6$)cycloalkyl, fluoro($C_3$–$C_6$)cycloalkyl and $C_4$–$C_{12}$ bicycloalkyl; and
(viii) the group represented by the following graphic formula:

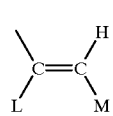

wherein L in graphic formula IIH may be hydrogen or $C_1$–$C_4$ alkyl and M in graphic formula IIH may be selected from the unsubstituted, mono-, and di-substituted members of the group consisting of naphthyl, phenyl, furanyl, and thienyl, each of said group substituents in this part (vii) being $C_1$–$C_4$ alkyl, $C_1$–$C_4$ alkoxy, fluoro, or chloro.

Alternatively, B and B' taken together may form fluoren-9-ylidene, mono-, or di-substituted fluoren-9-ylidene or form a member selected from the group consisting of saturated $C_3$–$C_{12}$ spiro-monocyclic hydrocarbon rings, e.g., cyclopropylidene, cyclobutylidene, cyclopentylidene, cyclohexylidene, cycloheptylidene, cyclooctylidene, cyclononylidene, cyclodecylidene cycloundecylidene, and cyclododecylidene, saturated $C_7$–$C_{12}$ spiro-bicyclic hydrocarbon rings, e.g., bicyclo[2.2.1]heptylidene, i.e., norbornylidene, 1,7,7-trimethyl bicyclo[2.2.1]heptylidene, i.e., bornylidene, bicyclo[3.2.1]octylidene, bicyclo[3.3.1] nonan-9-ylidene, bicyclo[4.3.2]undecane, and saturated $C_7$–$C_{12}$ spiro-tricyclic hydrocarbon rings, e.g., tricyclo [2.2.1.0$^{2,6}$]heptylidene, tricyclo[3.3.1.1$^{3,7}$]decylidene, i.e., adamantylidene, and tricyclo[5.3.1.1$^{2,6}$]dodecylidene, each of said fluoren-9-ylidene substituents being selected from the group consisting of $C_1$–$C_4$ alkyl, $C_1$–$C_4$ alkoxy, fluoro and chloro.

Preferably, B and B' are each selected from the group consisting of: (i) phenyl, mono-substituted phenyl, and di-substituted phenyl, preferably substituted in the meta and/or para positions; (ii) the unsubstituted, mono- and di-substituted aromatic heterocyclic groups furanyl, benzofuran-2-yl, thienyl, benzothien-2-yl and dibenzofuranyl, each of said phenyl and aromatic heterocyclic substituents in parts (i) and (ii) being selected from the group consisting of hydroxy, amino, mono($C_1$–$C_3$) alkylamino, di($C_1$–$C_3$)alkylamino, piperidino, morpholino, pyrryl, $C_1$–$C_3$ alkyl, $C_1$–$C_3$ chloroalkyl, $C_1$–$C_3$ fluoroalkyl, $C_1$–$C_3$ alkoxy, mono($C_1$–$C_3$)alkoxy($C_1$–$C_3$)alkyl, fluoro and chloro; (iii) the groups represented by the graphic formulae IIF and IIG, wherein A is methylene and D is oxygen, $R_{23}$ is $C_1$–$C_3$ alkyl or $C_1$–$C_3$ alkoxy, $R_{21}$ and $R_{22}$ are each hydrogen or $C_1$–$C_3$ alkyl; and q is the integer 0 or 1; (iv) $C_1$–$C_4$ alkyl; and (v) the group represented by the graphic formula IIH wherein L is hydrogen or methyl and M is phenyl or mono-substituted phenyl, said phenyl substituent being selected from the group consisting of $C_1$–$C_3$ alkyl, $C_1$–$C_3$ alkoxy, and fluoro; or (vi) B and B' taken together form fluoren-9-ylidene, mono-substituted fluoren-9-ylidene or a member selected from the group consisting of saturated $C_3$–$C_8$ spiro-monocyclic hydrocarbon rings, saturated $C_7$–$C_{10}$ spiro-bicyclic hydrocarbon rings, and saturated $C_7$–$C_{10}$ spiro-tricyclic hydrocarbon rings, said fluoren-9-ylidene substituent being selected from the group consisting of $C_1$–$C_3$ alkyl, $C_1$–$C_3$ alkoxy, fluoro and chloro.

More preferably, B and B' are each selected from the group consisting of (i) phenyl, mono- and di-substituted phenyl, (ii) the unsubstituted, mono- and di-substituted aromatic heterocyclic groups furanyl, benzofuran-2-yl, thienyl, benzothien-2-yl and dibenzofuranyl, each of said phenyl and aromatic heterocyclic substituents being selected from the group consisting of hydroxy, $C_1$–$C_3$ alkyl, $C_1$–$C_3$ alkoxy, fluoro and chloro; and (iii) the group represented by graphic formula IIF, wherein A is methylene and D is oxygen, $R_{23}$ is $C_1$–$C_3$ alkyl or $C_1$–$C_3$ alkoxy, $R_{21}$ and $R_{22}$ are each hydrogen or $C_1$–$C_3$ alkyl, and q is the integer 0 or 1; or (iv) B and B' taken together form fluoren-9-ylidene, adamantylidene, bornylidene, norbornylidene, or bicyclo [3.3.1]nonan-9-ylidene.

Compounds represented by graphic formula I, which have the substituents $R_1$–$R_4$, B and B' described hereinbefore, may be prepared by the following Reactions A through F. Methods for preparing compounds represented by graphic formula I wherein $R_3$ is an amino group are included in Reaction E. Preparation of Compound I wherein $R_3$ and $R_4$ together form a heterocyclic ring is described in Reaction F.

Methods for the preparation of compounds wherein $R_1$, $R_2$, B and/or B' is the polyalkoxylated group T are described in U. S. Pat. No. 5,961,842, which disclosure is incorporated herein by reference. Methods for the preparation of compounds wherein $R_1$, $R_2$, B and/or B' is the polymerizable polyalkoxylated group T are described in U. S. application Ser. No. 09/151,911, filed Sep. 11, 1998, which application is incorporated herein by reference.

Compounds represented by graphic formula V, VA, or VB are either purchased or prepared by Friedel-Crafts methods shown in Reaction A using an appropriately substituted or unsubstituted benzoyl chloride of graphic formula IV with a substituted or unsubstituted benzene compound of graphic formula III, which may be commercially available. See the publication *Friedel-Crafts and Related Reactions*, George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992.

In Reaction A, the compounds represented by graphic formulae III and IV are dissolved in a solvent, such as carbon disulfide or methylene chloride, and reacted in the presence of a Lewis acid, such as aluminum chloride or tin tetrachloride, to form the corresponding substituted benzophenone represented by graphic formula V (VA in Reaction B or VB in Reaction C). R and R' represent possible substituents, as described hereinbefore with respect to graphic formula I.

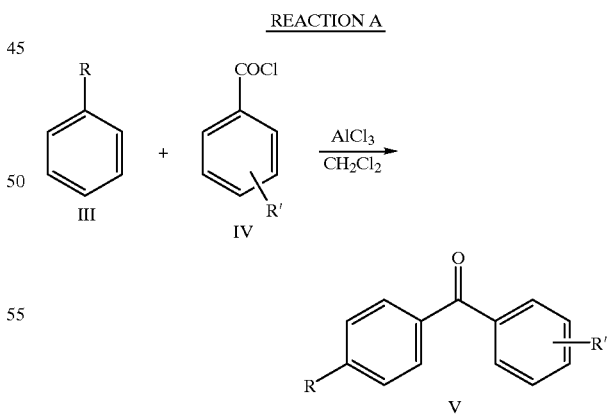

In Reaction B, the substituted or unsubstituted ketone represented by graphic formula VA, in which B and B' may represent groups other than substituted or unsubstituted phenyl, as shown in graphic formula V, is reacted with sodium acetylide in a suitable solvent, such as anhydrous tetrahydrofuran (THF), to form the corresponding propargyl alcohol represented by graphic formula VI. Propargyl alcohols having B or B' groups other than substituted and unsubstituted phenyl may be prepared from commercially available ketones or ketones prepared via reaction of an acyl halide with a substituted or unsubstituted benzene, naphthalene or heteroaromatic compound, e.g., 9-julolidinyl. Propargyl alcohols having a B or B' group represented by graphic formula IIH may be prepared by the methods described in U.S. Pat. No. 5,274,132, column 2, lines 40 to 68.

REACTION B

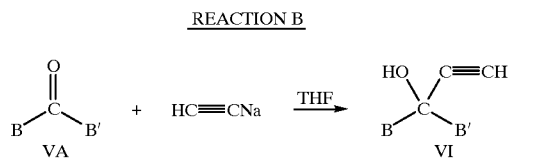

In Reaction C, a substituted benzophenone or benzaldehyde represented by graphic formula VB is reacted with an ester of succinic acid such as dimethyl succinate represented by graphic formula VII. Addition of the reactants to a solvent, e.g., toluene, containing potassium t-butoxide or sodium hydride as the base yields the Stobbe condensation half ester represented by graphic formula VIII. A mixture of cis and trans half esters forms which then undergoes cyclodehydration in the presence of acetic anhydride to form a mixture of acetoxynaphthalenes. Further purification to isolate the distinct isomer IX may be required. This product is hydrolyzed in methanol with hydrochloric acid to form the carbomethoxynaphthol represented by graphic formula X.

REACTION D

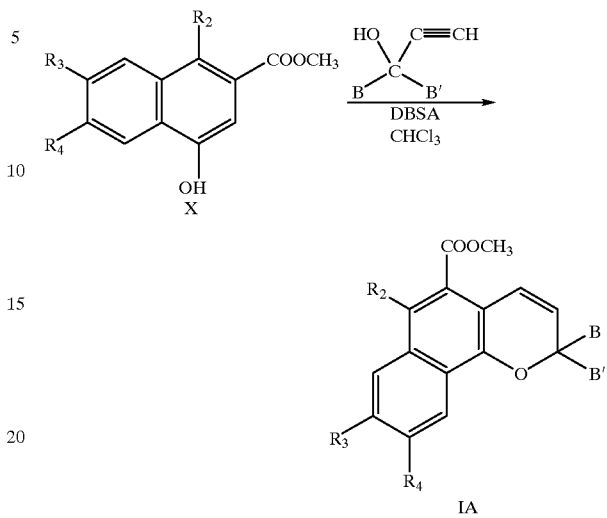

Reaction E along with the procedures described in Reactions C and D are followed to produce amino substituted naphthopyrans. In Reaction E, the ketone represented by graphic formula VC is reacted with a lithium salt of an amine represented by graphic formula XI in a solvent such as tetrahydrofuran (THF) to produce the amino substituted ketone represented by graphic formula XII. Treatment of

REACTION C

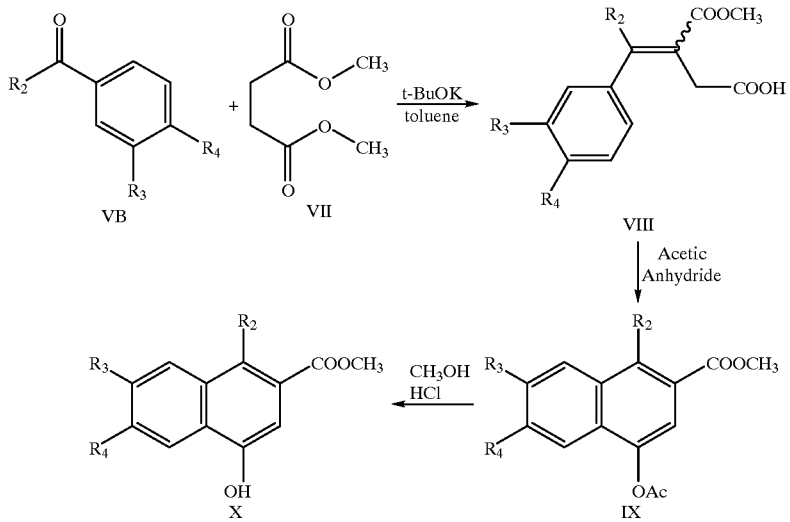

In Reaction D, the carbomethoxynaphthol represented by graphic formula X is coupled with a propargyl alcohol represented by graphic formula VI in the presence of a catalytic amount of an acid, e.g., dodecylbenzene sulfonic acid (DBSA), in a solvent, e.g., chloroform, to produce the naphthopyran represented by graphic formula IA.

compound XII with dimethyl succinate to produce the corresponding ester, followed by cyclization with acetic anhydride and subsequent methanolysis as described in Reaction C produces the corresponding amino substituted naphthol. The amino substituted naphthol is then coupled with propargyl alcohol as described in Reaction D to produce amino substituted naphthopyrans.

REACTION E

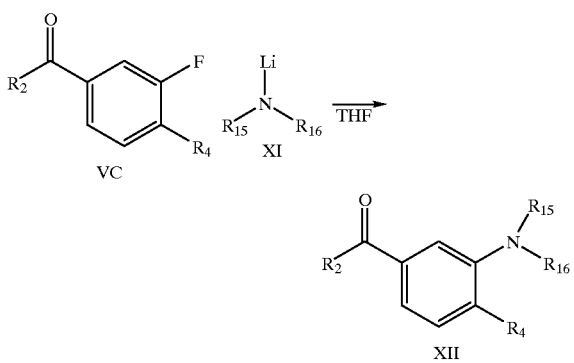

Reaction F along with the procedures described in Reactions C and D are followed to produce naphthopyrans having a heterocyclic ring fused thereto. In Reaction F, the compounds represented by graphic formulae XIII and XIV are dissolved in a solvent, such as carbon disulfide or methylene chloride, and reacted in the presence of a Lewis acid, such as aluminum chloride or tin tetrachloride, to form the corresponding substituted benzaldehyde, benzophenone, or acetophenone represented by graphic formula XV. Treatment of compound XV with dimethyl succinate to produce the corresponding ester, followed by cyclization with acetic anhydride and subsequent methanolysis as described in Reaction C produces the corresponding heterocyclic fused naphthol. The heterocyclic naphthol is then coupled with propargyl alcohol as described in Reaction D to produce heterocyclic fused naphthopyrans.

REACTION F

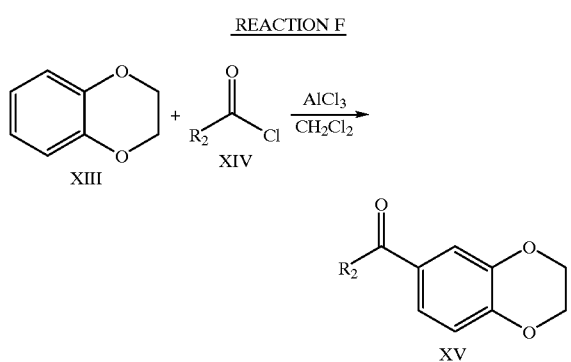

Compounds represented by graphic formula I may be used in those applications in which organic photochromic substances may be employed, such as optical lenses, e.g., vision correcting ophthalmic lenses, contact lenses and plano lenses, face shields, goggles, visors, camera lenses, windows, automotive windshields, aircraft and automotive transparencies, e.g., T-roofs, sidelights and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit blended color changes from colorless to colors of orange/brown to green. These blended color changes are a result of one absorption band (band "A") in the 420–500nm region and another absorption band (band "B") in the 480–620nm region Other than in the operating examples, or where otherwise indicated, all numbers expressing wavelengths, quantities of ingredients or reaction conditions used herein are to be understood as modified in all instances by the term "about".

Examples of contemplated naphthopyran compounds within the scope of the invention are the following:

(a) 2,2-di(4-methoxyphenyl)-5-methoxycarbonyl-6-(3,4-dimethoxyphenyl)-8,9-dimethoxy-2H-naphtho[1,2-b]pyran;

(b) 2,2-diphenyl-5-methoxycarbonyl-6-(3,4-dimethoxyphenyl)-8,9-dimethoxy-2H-naphtho[1,2-b]pyran;

(c) 2,2-di(4-methoxyphenyl)-5-methoxycarbonyl-6-phenyl-8,9-dimethoxy-2H-naphtho[1,2-b]pyran;

(d) 2,2-di(4-methoxyphenyl)-5-methoxycarbonyl-6-phenyl-9,10-dihydro-2H-[1,4]dioxino[2',3':8,9]naphtho[1,2-b]pyran;

(e) 2,2-di(4-methoxyphenyl)-5-methoxycarbonyl-6-phenyl-8-morpholino-9-methoxy-2H-naphtho[1,2-b]pyran;

(f) 2-(4-methoxyphenyl)-2-phenyl-5-methoxycarbonyl-8,9-dimethoxy-2H-naphtho[1,2-b]pyran;

(g) 2,2-diphenyl-5-methoxycarbonyl-8,9-dimethoxy-2H-naphtho[1,2-b]pyran;

(h) 2,2-di-(4-methoxyphenyl)-5-methoxycarbonyl-8,9-dimethoxy-2H-naphtho[1,2-b]pyran;

(i) 2,2-di(4-methoxyphenyl)-5-methoxycarbonyl-6-phenyl-8-piperidino-9-methoxy-2H-naphtho[1,2-b]pyran;

(j) 2,2-di(4-methoxyphenyl)-5-methoxycarbonyl-6-methyl-8,9-dimethoxy-2H-naphtho[1,2-b]pyran; and (k) 2,2-diphenyl-5-methoxycarbonyl-6-phenyl-2H-[1,3]dioxolo[4', 5':8,9]naphtho[1,2-b]pyran.

It is contemplated that the organic photochromic naphthopyrans of the present invention may be used alone, in combination with other naphthopyrans of the present invention, or in combination with one or more other appropriate complementary organic photochromic materials, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

Examples of complementary organic photochromic compounds include other naphthopyrans and indenonaphthopyrans, chromenes and oxazines, substituted 2H-phenanthro[4,3-b]pyran and 3H-phenanthro[1,2-b]pyran compounds, benzopyran compounds having substituents at the 2-position of the pyran ring and mixtures of such photochromic compounds. Such photochromic compounds are described in U.S. Pat. Nos. 3,562,172; 3,567,605; 3,578, 602; 4,215,010; 4,342,668; 4,816,584; 4,818,096; 4,826, 977; 4,880,667; 4,931,219; 5,066,818; 5,238,981; 5,274, 132; 5,384,077; 5,405,958; 5,429,774; 5,458,814; 5,466, 398; 5,514,817; 5,552,090; 5,552,091; 5,565,147; 5,573, 712; having a thickness ranging from 1 to 50 microns may be applied by conventional methods used in coating technology. Coatings of a thickness greater than 50 microns may require molding methods typically used for overlays. A preferred coating composition is polyurethane prepared from organic polyol(s).

The complementary organic photochromic materials may also include polymerizable photochromic compounds, such as those disclosed in U.S. Pat. Nos. 4,719,296; 5,166,345; 5,236,958; 5,252,742; 5,359,035; and 5,488,119.

Other complementary photochromic substances contemplated are metal-dithiozonates, e.g., mercury dithizonates which are described in, for example, U.S. Pat. No. 3,361,706; and fulgides and fulgimides, e.g., the 3-furyl and 3-thienyl fulgides and fulgimides, which are described in U.S. Pat. No. 4,931,220 at column 20, line 5 through column 21, line 38.

The disclosures relating to such photochromic compounds in the aforedescribed patents are incorporated herein, in toto, by reference. The photochromic articles of the present invention may contain one photochromic compound or a mixture of photochromic compounds, as desired.

The photochromic compounds of the present invention may be associated with a polymeric organic host material or other substrate by various means. They may be incorporated, i.e., dissolved and/or dispersed, into the host material, polymerized with other components of the host material, and/or incorporated into a coating applied to a substrate, e.g., a polymeric coating applied to one surface of the polymeric organic host material.

Each of the photochromic substances described herein may be used in amounts (or in a ratio) such that an organic host material or substrate to which the photochromic compounds or mixture of compounds is associated, exhibits a desired resultant color, e.g., a substantially neutral color when activated with unfiltered sunlight, i.e., as near a neutral color as possible given the colors of the activated photochromic compounds. Neutral gray and neutral brown colors are preferred. Further discussion of neutral colors and ways to describe colors may be found in U.S. Pat. No. 5,645,767 column 12, line 66 to column 13, line 19.

The amount of the photochromic naphthopyrans to be applied to or incorporated into a coating composition or host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic compounds. Typically, the more photochromic compound applied or incorporated, the greater is the color intensity up to a certain limit.

The relative amounts of the aforesaid photochromic compounds used will vary and depend in part upon the relative intensities of the color of the activated species of such compounds, the ultimate color desired and the method of application to the host material or substrate. Generally, the amount of total photochromic compound incorporated into or applied to a photochromic optical host material may range from about 0.05 to about 2.0, e.g., from 0.2 to about 1.0, milligrams per square centimeter of surface to which the photochromic compound is incorporated or applied. The amount of photochromic material incorporated into a coating composition may range from 0.1 to 40 weight percent based on the weight of the liquid coating composition.

The photochromic naphthopyrans of the present invention may be associated with the host material by various methods described in the art. See, for example, column 13, lines 40 to 58 of U.S. Pat. No. 5,645,767. Aqueous or organic solutions of the photochromic compounds may be used to incorporate the photochromic compounds into a polymeric organic host material or other materials such as textiles and polymeric coating compositions. Polymeric coating compositions may be applied to the substrate using a coating process such as that described in U.S. Pat. No. 3,971,872, the disclosure of which is incorporated herein by reference.

Application of the polymeric coating may be by any of the methods used in coating technology such as, for example, spray coating, spin coating, spread coating, curtain coating, dip coating, casting or roll-coating and methods used in preparing overlays, such as the method of the type described in U.S. Pat. No. 4,873,029, which is incorporated herein by reference. The application method selected also depends on the thickness of the cured coating. Coatings having a thickness ranging from 1 to 50 microns may be applied by conventional methods used in coating technology. Coatings of a thickness greater than 50 microns may require molding methods typically used for overlays. A preferred coating composition is polyurethane prepared from organic polyol(s) and an isocyanate. The photochromic substances of the present invention may be dissolved or dispersed within the organic polyol component or isocyanate component of the polyurethane coating or may be added to a mixture of the polyurethane-forming components.

The host material will usually be transparent, but may be translucent or even opaque. The host material need only be pervious to that portion of the electromagnetic spectrum, which activates the photochromic substance, i.e., that wavelength of ultraviolet (UV) light that produces the open or colored form of the substance and that portion of the visible spectrum that includes the absorption maximum wavelength of the substance in its UV activated form, i.e., the open form. Preferably, the host color should not be such that it masks the color of the activated form of the photochromic compounds, i.e., so the change in color is readily apparent to the observer. Compatible tints may be applied to the host material as described in U.S. Pat. No. 5,645,767 in column 13, line 59 to column 14, line 3.

Most preferably, the polymeric organic host material is a solid transparent or optically clear material, e.g., materials suitable for optical applications, such as plano, ophthalmic and contact lenses, windows, automotive transparencies, e.g., windshields, aircraft transparencies, plastic sheeting, polymeric films, etc.

Examples of polymeric organic host materials which may be used with the photochromic compounds described herein include: polymers, i.e., homopolymers and copolymers, of the bis(allyl carbonate) monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, mono- or polyfunctional, e.g., di- or multi-functional, acrylate and/or methacrylate monomers, poly($C_1C_{12}$ alkyl methacrylates), such as poly (methyl methacrylate), poly(oxyalkylene) dimethacrylate, poly (alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, polythiourethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate. Further examples of polymeric organic host materials are disclosed in the U.S. Pat. No. 5,753,146, column 8, line 62 to column 10, line 34, which disclosure is incorporated herein by reference.

Transparent copolymers and blends of transparent polymers are also suitable as host materials. Preferably, the host material or substrate for the photochromic polymeric coating composition is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polythiourethanes, polymers of members of the group consisting of diethylene glycol dimethacrylate monomers, diisopropenyl benzene monomers, ethoxylated bisphenol A dimethacrylate monomers, ethylene glycol bis-methacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly contemplated is use of the photochromic naphthopyrans of the present invention with optical organic resin monomers used to produce optically clear coatings and polymerizates, i.e., materials suitable for optical applications, such as lenses for use in a pair of spectacles, e.g., plano or ophthalmic spectacle lenses, or for use as contact lenses. Optically clear polymerizates may have a refractive index that may range from about 1.35 to about 1.75, e.g., from about 1.495 to about 1.66.

Specifically contemplated are polymerizates of optical resins sold by PPG Industries, Inc. under the CR-designation, e.g., CR-307 and CR-407, and polymerizates prepared for use as hard or soft contact lenses. Methods for producing both types of contact lenses are disclosed in U.S. Pat. No. 5,166,345, column 11, line 52, to column 12, line 52, which disclosure is incorporated herein by reference. Additional polymerizates contemplated for use with the photochromic hydroxylated/carboxylated naphthopyrans of the present invention are polymerizates used to form soft contact lenses with high moisture content described in U.S. Pat. No. 5,965,630 and extended wear contact lenses described in U.S. Pat. No. 5,965,631, both disclosures of which are incorporated herein by reference.

More particularly, contemplated is use of the photochromic naphthopyrans of the present invention with optical organic resin monomers used to produce optically clear coatings and polymerizates, i.e., materials suitable for optical applications, such as for example piano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the designation CR-307 and CR-407.

The present invention is more particularly described in the following examples which are intended as illustrative only, since numerous modifications and variations therein will be apparent to those skilled in the art.

EXAMPLE 1

Step 1

1,2-Dimethoxybenzene (74.5 grams) and a solution of 3,4-dimethoxybenzoyl chloride (98.2 grams) in 500 milliliters (mL) of methylene chloride were added to a reaction flask fitted with a solid addition funnel under a nitrogen atmosphere. Solid anhydrous aluminum chloride (71.8 grams) was added portionwise to the reaction mixture with occasionally cooling of the reaction mixture in an ice/water bath. The reaction mixture was stirred at room temperature for 3 hours. The resulting mixture was poured into 300 mL of a 1:1 mixture of ice and 1N hydrochloric acid and stirred vigorously for 15 minutes. The mixture was extracted twice with 100 mL methylene chloride. The organic layers were combined and washed with 50 mL of 10 weight percent sodium hydroxide followed by 50 mL of water. The solvent was removed by rotary evaporation to give a yellow solid. Recrystallization from 95 percent ethanol yielded 127 grams of beige needles having a melting point of 146–147° C. A nuclear magnetic resonance (NMR) spectrum showed the product to have a structure consistent with 3,3',4,4'-tetramethoxybenzophenone.

Step 2

Potassium t-butoxide (55.4 grams) and 100.0 grams of the product from Step 1 were added to a reaction flask containing 600 mL of toluene under a nitrogen atmosphere. The mixture was heated to reflux and dimethyl succinate (193 grams) was added dropwise over a 1 hour period. The mixture was refluxed for 5 hours and cooled to room temperature. The resulting precipitate was collected by vacuum filtration and washed with fresh toluene to yield 143 grams of a beige powder. The powder was dissolved in about 200 mL of water and acidified to pH 2 with 4N hydrochloric acid. The acidic solution was extracted five times with 50 mL of methylene chloride. The organic extracts were combined and concentrated by rotary evaporation to produce 102 grams of a thick brown oil. An NMR spectrum showed the desired product to have a structure consistent with 4,4-di(3,4-dimethoxyphenyl)-3-methoxycarbonyl-3-butenoic acid. This material was not purified further but was used directly in the next step.

Step 3

The crude half-ester from Step 2 (100 grams), 60 mL of acetic anhydride, and 300 mL of toluene were added to a reaction flask under a nitrogen atmosphere. The reaction mixture was heated to 110° C. for 6 hours and cooled to room temperature, and the solvents (toluene and acetic anhydride) were removed by rotary evaporation. The residue was dissolved in 300 mL of methylene chloride and 200 mL of water. Solid sodium carbonate was added to the biphasic mixture until bubbling ceased. The layers separated and the aqueous layer was extracted with two 50 mL portions of methylene chloride. The organic layers were combined and the solvent (methylene chloride) was removed by rotary evaporation to yield a thick red oil. The oil was dissolved in warm methanol and chilled at 0° C. for 2 hours. The resulting crystals were collected by vacuum filtration, washed with cold methanol to produce 38.9 grams of a product having a melting point of 176–177° C. An NMR spectrum showed the product to have a structure consistent with 1-(3,4-dimethoxyphenyl)-2-methoxycarbonyl-4-acetoxy-6,7-dimethoxynaphthalene.

Step 4

1-(3,4-Dimethoxyphenyl)-2-methoxycarbonyl-4-acetoxy-6,7-dimethoxynaphthalene from Step 3 (5 grams), 5 mL of 12M hydrochloric acid, and 30 mL of methanol were combined in a reaction flask and heated to reflux for 1 hour. The reaction mixture was cooled and the resulting precipitate was collected by vacuum filtration and washed with cold methanol yielding 2.1 grams of beige needles having a melting point of 213–214° C. An NMR spectrum showed the product to have a structure consistent with 1-(3,4-dimethoxyphenyl)-2-methoxycarbonyl-4-hydroxy-6,7-dimethoxynaphthalene.

Step 5

1-(3,4-Dimethoxyphenyl)-2-methoxycarbonyl-4-hydroxy-6,7-dimethoxy-naphthalene from Step 4 (1.0 grams), 1,1-di(4-methoxyphenyl-2-propyn-1-ol (0.9 grams), dodecylbenzene sulfonic acid (about 10 milligrams, and 50 mL of chloroform were combined in a reaction vessel and stirred at ambient temperature for 1 hour. The solvent was removed by rotary evaporation and the resulting brown solid recrystallized from hot 2-propanol. Beige needles (1.17 grams, having a melting point of 202–204° C.) were collected by vacuum filtration. NMR analysis showed the product to have a structure consistent with 2,2-di(4-methoxyphenyl)-5-methoxycarbonyl-6-(3,4-dimethoxyphenyl)-8,9-dimethoxy-2H-naphtho[1,2-b]pyran.

EXAMPLE 2

The process of Example 1 was followed except that 500 milligrams of 1-(3,4-dimethoxyphenyl)-2-methoxycarbonyl-4-hydroxy-6,7-dimethoxynaphthalene (Example 1, Step 4) was used, 1,1-diphenyl-2-propyn-1-ol (285 milligrams) was used instead of 1,1-di(4-methoxyphenyl)-2-propyn-1-ol and 15 mL of methylene chloride were combined in a reaction vessel and stirred at ambient temperature overnight. The reaction mixture was diluted with methylene chloride (30 mL) and washed with 5 mL of a 1N aqueous NaOH and washed again with water (10 mL). The product was dried over anhydrous sodium sulfate, filtered and the filtrate was concentrated by rotary evaporation. The resulting brown solid recrystallized from hot 2-propanol. Upon vacuum filtration, 293 milligrams of yellow rosettes having a melting point of 232–234° C. were collected. An NMR spectrum showed the product to have a structure consistent with 2,2-diphenyl-5-methoxycarbonyl-6-(3,4-dimethoxyphenyl)-8,9-dimethoxy-2H-naphtho[1,2-b]pyran.

EXAMPLE 3

Step 1

The process of Step 1 of Example 1 was followed except that 92.5 grams of 1,2-dimethoxy benzene was used; benzoyl chloride (84.3 grams) was used instead of 3,4-dimethoxy benzoyl chloride and 89.7 grams of aluminum chloride was used. The product (147 grams) had a melting point of 103–105° C. An NMR spectrum showed the product to have a structure consistent with 3,4-dimethoxy benzophenone.

Step 2

The process of Step 2 of Example 1 was followed except that 3,4-dimethoxybenzophenone (90 grams) was used in place of 3,3',4,4'-tetramethoxybenzophenone, 144.8 grams of dimethyl succinate (dissolved in 300 mL of toluene), 62 grams of potassium t-butoxide, and 700 mL of toluene were used. Instead of isolating the precipitate, 300 mL of water was added to the reaction mixture and vigorously stirred for 20 minutes. The layers separated and the organic phase was extracted with 100 mL portions of water three times, and the combined aqueous layers were washed with 50 mL portions of chloroform three times. The aqueous layer was acidified to pH 2 with 6N hydrochloric acid and a precipitate formed. The aqueous layer was extracted with three 100 mL portions of chloroform. The organic extracts were combined and concentrated by rotary evaporation. An NMR spectrum of the resulting oil showed the product to have structures consistent with a mixture of (E and Z) 4-(3,4-dimethoxyphenyl)-4-phenyl-3-methoxycarbonyl-3-butenoic acids.

Step 3

The process of Example 1, Step 3, was followed using the oil containing (E and Z) 4-(3,4-dimethoxyphenyl)-4-

(phenyl)-3-methoxycarbonyl-3-butenoic acids (8.6 grams) which was added to a reaction flask containing acetic anhydride (5 mL) and toluene (50 mL). An NMR spectrum showed the recovered solid product to have structures consistent with a mixture of 1-(3,4-dimethoxyphenyl)-2-methoxycarbonyl-4-acetoxynaphthalene and 1-phenyl-2-methoxycarbonyl-4-acetoxy-6,7-dimethoxynaphthalene. The product mixture was used without further purification in subsequent reactions.

Step 4

The process of Example 1, Step 4 was followed except that a mixture of 1-(3,4-dimethoxyphenyl)-2-methoxycarbonyl-4-acetoxynaphthalene and 1-phenyl-2-methoxycarbonyl-4-acetoxy-6,7-dimethoxynaphthalene was used. The product was purified by filtering through a plug of silica gel using a 2:1 mixture of hexane and ethyl acetate as the elutant. Concentration of the filtrate by rotary evaporation yielded 3.3 grams of a beige solid. An NMR spectrum showed the product to have structures consistent with a mixture of 1-(3,4-dimethoxyphenyl)-2-methoxycarbonyl-4-hydroxynaphthalene and 1-phenyl-2-methoxycarbonyl-4-hydroxy-6,7-dimethoxynaphthalene.

Step 5

A mixture of 1-phenyl-2-methoxycarbonyl-4-hydroxy-6,7-dimethoxynaphthalene and 1-(3,4-dimethoxyphenyl)-2-methoxycarbonyl-4-hydroxynaphthalene from Step 4 (3.0 grams), 1,1-di(4-methoxyphenyl)-2-propyn-1-ol (2.3 grams), dodecylbenzene sulfonic acid (about 10 milligrams), and 50 mL of chloroform were combined in a reaction vessel and stirred at ambient temperature for 1 hour. The solvent was removed by rotary evaporation and the resulting brown solid chromatographed on silica gel (using a 3:1 mixture of hexane and ethyl acetate as the elutant. Recrystallization from ethanol (95%) yielded 1.15 grams of a first product having a melting point of 185–186° C. and 846 milligrams of a second product having a melting point range of 110–115° C. An NMR spectrum showed the first recovered product to have a structure consistent with 2,2-di(4-methoxyphenyl)-5-methoxycarbonyl-6-phenyl-8,9-dimethoxy-[2H]-naphtho[1,2-b]pyran. NMR spectrum showed that the second recovered product had a structure consistent with 2,2-di(4-methoxyphenyl)-5-methoxycarbonyl-6-(3,4-dimethoxyphenyl)-2H-naphtho[1,2-b]pyran. The second product was isolated and used as Comparative Example 2 described hereinafter.

EXAMPLE 4

Step 1

2,3-Dihydrobenzo[b](1,4)dioxin (50 grams) and a solution of benzoyl chloride (55 grams) in 300 milliliters (mL) of methylene chloride were added to a reaction flask fitted with a solid addition funnel under a nitrogen atmosphere. Solid anhydrous aluminum chloride (54 grams) was added to the reaction mixture with occasionally cooling of the reaction mixture in an ice/water bath. The reaction mixture was stirred at room temperature for 3 hours. The resulting mixture was poured into 300 mL of a 1:1 mixture of ice and 1N hydrochloric acid and stirred vigorously for 15 minutes. The mixture was extracted twice with 100 mL methylene chloride. The organic layers were combined and washed with 50 mL of 10 weight percent sodium hydroxide followed by 50 mL of water. The solvent was removed by rotary evaporation to give a yellow solid. Recrystallization from hexane yielded 70 grams of white solid. A nuclear magnetic resonance (NMR) spectrum showed the product to have a structure consistent with 2,3-dihydrobenzo[b][1,4]dioxin-6-yl-phenyl-1-methanone.

Step 2

Potassium t-butoxide (30 grams) and 50.0 grams of the product from Step 1 were added to a reaction flask containing 300 mL of toluene under a nitrogen atmosphere. The mixture was heated to reflux and dimethyl succinate (75 grams) was added dropwise over a 1 hour period. The mixture was refluxed for 5 hours and cooled to room temperature. 500 mL of water was added and the mixture stirred for 30 minutes. The aqueous layer was separated and washed with toluene. The aqueous layer was acidified to pH 2 with 4N hydrochloric acid. The acidic solution was extracted five times with 50 mL of methylene chloride. The organic extracts were combined and concentrated by rotary evaporation to produce 70 grams of a thick brown oil. An NMR spectrum showed the desired product to have a structure consistent with 4-phenyl-4-(2,3-dihydrobenzo[b][1,4]dioxin-6-yl)-3-methoxycarbonyl-3-butenoic acid. This material was not purified further but was used directly in the next step.

Step 3

The crude half-ester from Step 2 (70 grams), and 120 mL of acetic anhydride were added to a reaction flask under a nitrogen atmosphere. The reaction mixture was heated to reflux for 4 hours and cooled to room temperature, and the solvents (acetic anhydride) were removed by rotary evaporation to yield a thick oil. An NMR spectrum showed the product to have a structure consistent with a mixture of 1-(2,3-dihydrobenzo[b][1,4]dioxin-6-yl)-2-methoxycarbonyl-4-acetoxynaphthalene and 9-phenyl-8-methoxycarbonyl-6-acetoxy-2,3-dihydronaphtho[2,3-b][1,4]dioxin. This material was not purified further but was used directly in the next step.

Step 4

The crude acetoxy mixture from Step 3, 5 mL of 12M hydrochloric acid, and 200 mL of methanol were combined in a reaction flask and heated to reflux for 1 hour. The reaction mixture was cooled and the resulting precipitate was collected by vacuum filtration and washed with cold methanol yielding 15 grams of light yellow solid. An NMR spectrum showed the roduct to have structure consistent with 9-phenyl-8-ethoxycarbonyl-6-hydroxy-2,3-dihydronaphtho[2,3-b][1,4]dioxin-6-ol.

Step 5

A reaction flask was charged with 9-phenyl-8-ethoxycarbonyl-6-hydroxy-2,3-dihydronaphtho[2,3-b][1,4]dioxin-6-ol from Step 4 (2.0 grams), 1,1-di(4-methoxyphenyl-2-propyn-1-ol (0.9 grams), p-toluene sulfonic acid (about 10 milligrams), and 50 mL of chloroform and the mixture stirred at ambient temperature for 4 hours. The solvent was removed by rotary evaporation and the resulting brown solid recrystallized from diethyl ether. The crystals (1.17 grams, having a melting point of 210–212° C.) were collected by vacuum filtration. NMR analysis showed the product to have a structure consistent with 2,2-di(4-methoxyphenyl)-5-methoxycarbonyl-6-phenyl-9,10-dihydro-2H-[1,4]dioxino[2',3':8,9]naphtho[1,2-b]pyran.

EXAMPLE 5

Step 1

The process of Example 4, Step 1 was followed except that 2-fluoroanisole was used in place of 2,3-dihydrobenzo[b][1,4]dioxin. The desired product was separated by crystallization using hexane:diethyl ether mixture (1:1) as the solvent. The yield obtained was 30 grams. An NMR spectrum showed the product to have a structure consistent with 3-fluoro-4-methoxybenzophenone.

Step 2

3-Fluoro-4-methoxybenzophenone from Step 2 (25 grams), 20 grams of 4-morpholinyl lithium, 100 ml of anhydrous tetrahydrofuran were added to a reaction flask under a nitrogen atmosphere. The reaction mixture was heated to reflux for 4 hours and cooled to room temperature. The resulting mixture was poured into 300 mL of a 1:1 mixture of ice and 5% hydrochloric acid and stirred vigorously for 15 minutes. The mixture was extracted twice with 100 mL methylene chloride. The organic layers were combined and washed with 50 mL of water. The solvent was removed by rotary evaporation to give a white solid. Recrystallization from hexane yielded 20 grams of white solid. A nuclear magnetic resonance (NMR) spectrum showed the product to have a structure consistent with 3-morpholino-4-methoxybenzophenone.

Step 3

The process of Example 4, from Step 2 to Step 5 were followed except that in Step 2, 3-morpholino-4-methoxybenzophenone was used in place of 2,3-dihydrobenzo[b][1,4]dioxin-6-yl-phenyl-1-methanone. The recovered crystals, 1.5 grams, had a melting point of 188 to 190° C. A nuclear magnetic resonance (NMR) spectrum showed the product to have a structure consistent with 2,2-di(4-methoxyphenyl)-5-methoxycarbonyl-6-phenyl-8-morpholino-9-methoxy-2H-naphtho[1,2-b]pyran.

EXAMPLE 6

Step 1

Potassium t-butoxide (15.0 grams) was weighed into a reaction flask equipped with a mechanical stirrer and placed under a nitrogen atmosphere. 100 Milliliters (mL) of toluene was added and the reaction mixture was heated to the reflux temperature. A mixture of 3,4-dimethoxybenzaldehyde (16.6 grams) and dimethylsuccinate (18.1 grams) in 80 mL of toluene was added over a 30 minute period, accompanied by vigorous stirring, to the heated reaction mixture. After the addition, the temperature of the reaction mixture was maintained at reflux for 90 minutes. After cooling the reaction mixture to room temperature, it was poured into 500 mL of water and the toluene layer was separated. The aqueous layer was extracted with toluene (200 mL) and acidified with concentrated hydrochloric acid. A brownish oily solid precipitate formed and was recovered from the acidified aqueous layer. The recovered oily solid was extracted three times, each time with 200 mL of ethyl acetate. The organic layers were combined, washed with saturated NaCl solution (300 mL) and dried over anhydrous sodium sulfate. Removal of the solvent by rotary evaporation yielded 25 grams of a brownish oily solid product. A nuclear magnetic resonance (NMR) spectrum showed the product to have a structure consistent with a mixture of (E and Z) 4-(3,4-dimethoxyphenyl)-3-methoxycarbonyl-3-butenoic acids. This material was not purified further but was used directly in the next step.

Step 2

The oily solid containing the E and Z isomers from Step 1 was placed in a reaction flask. Acetic anhydride (40 mL) and 3.9 grams of sodium acetate were added. The reaction mixture was heated to the reflux temperature for 2 hours and cooled to 0° C. A yellow solid formed and was recovered by filtration. The recovered product was dried under vacuum to obtain 8.3 grams of product. An NMR spectrum showed the product to have a structure consistent with 2-methoxycarbonyl-4-acetoxy-6,7-dimethoxynaphthalene. This material was not purified further but was used directly in the next step.

Step 3

2-Methoxycarbonyl-4-acetoxy-6,7-dimethoxynaphthalene from Step 2 (8.0 grams) and 100 mL of methanol were combined in a reaction flask. Concentrated hydrochloric acid (1.5 mL) was added to the reaction flask. The contents of the reaction flask was heated to reflux for 3 hours under a nitrogen atmosphere. The reaction mixture was cooled to 0° C. Yellow crystals formed and were recovered by filtration. The recovered crystals were dried under vacuum to yield 6.2 grams of product. An NMR spectrum showed the product to have a structure consistent with 2-methoxycarbonyl-4-hydroxy-6,7-dimethoxynaphthalene. This material was not purified further but was used directly in the next step.

Step 4

2-Methoxycarbonyl-4-hydroxy-6,7-dimethoxynaphthalene from Step 3 (1.70 grams), 1-(4-methoxyphenyl)-1-phenyl-2-propyn-1-ol (1.5 grams), dodecylbenzene sulfonic acid (about 20 milligrams), and 100 mL of methylene chloride were combined in a reaction vessel and stirred at ambient temperature for 2 hours. The solvent was removed by rotary evaporation. The remaining brown solid was purified by recrystallization from acetone to get 2.1 grams of a white solid product. NMR analysis showed the product to have a structure consistent with 2-(4-methoxyphenyl)-2-phenyl-5-methoxycarbonyl-8,9-dimethoxy-2H-naphtho[1,2-b]pyran.

EXAMPLE 7

The process of Step 4, Example 6 was followed except that 1,1-diphenyl-2-propyn-1-ol (0.95 grams) was used instead of 1-(4-methoxyphenyl)-1-phenyl-2-propyn-1-ol, 1.2 grams of 2-methoxycarbonyl-4-hydroxy-6,7-dimethoxynaphthalene and 80 mL of methylene chloride were used. The solvent was removed by rotary evaporation. The remaining brownish solid was purified by recrystallization from acetone to get 1.5 grams of a white solid product. NMR analysis showed the product to have a structure consistent with 2,2-diphenyl-5-methoxycarbonyl-8,9-dimethoxy-2H-naphtho[1,2-b]pyran.

EXAMPLE 8

The process of Step 4, Example 6 was followed except that 1,1-di(4-methoxyphenyl-2-propyn-1-ol (0.95 grams) was used instead of 1-(4-methoxyphenyl)-1-phenyl-2-propyn-1-ol, 0.93 grams of 2-methoxycarbonyl-4-hydroxy-6,7-dimethoxynaphthalene and 50 mL of methylene chloride were used. The solvent was removed by rotary evaporation. The remaining brownish solid was purified by recrystallization from acetone to get 1.2 grams of a white solid product. NMR analysis showed the product to have a structure consistent with 2,2-di-(4-methoxyphenyl)-5-methoxycarbonyl-8,9-dimethoxy-2H-naphtho[1,2-b]pyran.

COMPARATIVE EXAMPLES 1–3

Three naphtho[1,2-b]pyrans lacking a pair of adjacent substituents at the 7- and 8-, 8- and 9- or 9- and 10-positions of the naphthopyran ring were prepared following similar processes to those of Examples 1–5. The compounds of the Comparative Examples were determined to be:

(1) 2,2-di(4-methoxyphenyl)-5-methoxycarbonyl-6-(4-methoxyphenyl)-9-methoxy-2H-naphtho[1,2-b]pyran;
(2) 2,2-di(4-methoxyphenyl)-5-methoxycarbonyl-6-(3,4-dimethoxyphenyl)-2H-naphtho[1,2-b]pyran; and
(3) 2-(4-methoxyphenyl)-2-(4-dimethylaminophenyl)-5-methyl-7,9-dimethoxy-2H-naphtho[1,2-b]pyran.

EXAMPLE 9

PART A

Testing was done with the photochromic compounds described in Examples 1 through 8 and Comparative Examples 1 through 3 in the following manner. A quantity of photochromic compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating, if necessary. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour interval and then hold it at 60° C. for 16 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were conditioned, i.e., exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 250 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliwatts per square centimeter (mW/cm2). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density ($\Delta$OD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\%Ta)$, where %Ta is the percent transmittance in the activated state and the logarithm is to the base 10.

The optical properties of the photochromic compounds in the test squares are reported in Table 1. The $\Delta$OD/Min, which represents the sensitivity of the photochromic compound's response to UV light, was measured over the first five (5) seconds of UV exposure, then expressed on a per minute basis. The saturation optical density ($\Delta$OD@ Saturation) was taken under identical conditions as the $\Delta$OD/Min, except UV exposure was continued for 15 minutes.

The lambda max (Vis) is the wavelength in the visible spectrum at which the maximum absorption of the activated (colored) form of the photochromic compound in a test square occurs. The lambda max (Vis) wavelengths reported in Table 1 were determined by testing the photochromic test square polymerizates of Part A in a Varian Cary 3 uv-visible spectrophotometer. The bleach rate (T 1/2) is the time interval in seconds for the absorbance of the activated form of the photochromic compound in the test squares to read one half the highest absorbance at room temperature (72° F., 22.2° C.) after removal of the source of activating light.

Each of the compounds of the Examples and the Comparative Examples exhibited dual peak absorptions in the visible spectrum (lambda max visible) in distinct color regions. For each lambda max visible, the corresponding optical density (ΔOD/Min, and ΔOD at saturation), for the compounds of the Examples and Comparative Examples are tabulated in Table 1 for the two bands (A and B) of peak absorption for each compound. Table 1 also includes the bleach rate (T 1/2) for each of the compounds as measured at band A. The ratings of the Relative ΔOD at Saturation Test for the bands A and B of each of the Examples and Comparative Examples are calculated as follows: ΔOD at saturation (Band A)/ΔOD at saturation (Band B)×100. The ratings of the Relative ΔOD at Saturation Test for each of the compounds is tabulated in Table 2.

TABLE 1

| Compound Example | Sensitivity ΔOD/MIN | ΔOD @ Saturation | Bleach Rate T ½ sec | λ MAX (nm) Vis |
|---|---|---|---|---|
| 1 (Band A) | 0.12 | 0.25 | 124 | 454 |
| 1 (Band B) | 0.05 | 0.17 |  | 535 |
| 2 (Band A) | 0.11 | 0.89 | 415 | 429 |
| 2 (Band B) | 0.09 | 0.44 |  | 518 |
| 3 (Band A) | 0.20 | 0.33 | 100 | 454 |
| 3 (Band B) | 0.07 | 0.23 |  | 532 |
| 4 (Band A) | — | 0.38 | 155 | 445 |
| 4 (Band B) | 0.16 | 0.41 |  | 523 |
| 5 (Band A) | 0.27 | 0.59 | 131 | 481 |
| 5 (Band B) | 0.08 | 0.22 |  | 573 |
| 6 (Band A) | 0.24 | 0.23 | 47 | 443 |
| 6 (Band B) | 0.15 | 0.14 |  | 498 |
| 7 (Band A) | 0.33 | 0.47 | 80 | 426 |
| 7 (Band B) | 0.14 | 0.21 |  | 484 |
| 8 (Band A) | 0.17 | 0.10 | 27 | 452 |
| 8 (Band B) | 0.13 | 0.08 |  | 507 |
| Comp. Ex. 1 (Band A) | 0.05 | 0.15 | 82 | 439 |
| Comp. Ex. 1 (Band B) | 0.13 | 0.23 |  | 542 |
| Comp. Ex. 2 (Band A) | 0.04 | 0.08 | 77 | 422 |
| Comp. Ex. 2 (Band B) | 0.19 | 0.25 |  | 525 |
| Comp. Ex. 3 (Band A) | 0.09 | 0.19 | 105 | 494 |
| Comp. Ex. 3 (Band B) | 0.14 | 0.29 |  | 594 |

TABLE 2

| Compound Example | Relative Δ OD at Saturation |
|---|---|
| 1 | 147 |
| 2 | 202 |
| 3 | 143 |
| 4 | 93 |
| 5 | 268 |
| 6 | 164 |
| 7 | 223 |
| 8 | 125 |
| Comp. Ex. 1 | 62 |
| Comp. Ex. 2 | 35 |
| Comp. Ex. 3 | 66 |

The data presented in Tables 1 and 2 show that each tested compound of the present invention has two absorption peaks in the visible spectrum and a rating greater than 80 in the Relative ΔOD at Saturation Test.

This data demonstrates that a single compound of the present invention exhibits a blended activated hue. In the preparation of photochromic articles with a desired activated hue, a combination of complementary photochromic compounds each having an activated visible absorption maximum may be used. The activated visible absorption maxima of the various compounds are thereby blended to achieve the desired activated color. By employing a compound of the present invention having two activated visible absorption maxima, fewer distinct compounds are required to achieve a blend of activated visible absorption maxima to produce the desired activated hue, e.g. neutral color. In addition, the blended activated hue of a compound of the present invention is particularly suitable for use in photochromic articles having a brown activated hue due to the greater optical density of band A (420–500 nm) than the optical density of band B (480–620 nm).

The present invention has been described with reference to specific details of particular embodiments thereof. It is not intended that such details be regarded as limitations upon the scope of the invention except insofar as to the extent that they are included in the accompanying claims.

We claim:

1. A naphthopyran compound of 2H-naphtho[1,2-b]pyran structure, represented by the following graphic formula I:

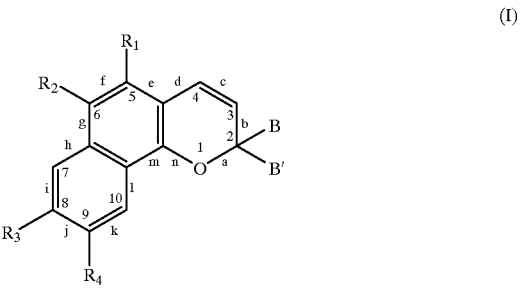

(I)

wherein, (a) in the 5 position, a group $R_1$ selected from:
   (i) group T represented by the formula:

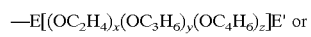

wherein —E— is —C(O)— or —CH$_2$—, E' is $C_1$–$C_3$ alkoxy or a polymerizable group, x, y and z are each a number between 0 and 50, and the sum of x, y and z is between 2 and 50; or (ii) the group consisting of —CH$_2$X, —C(V)$_2$X or —C(O)Y, wherein: X is hydrogen, $C_1$–$C_6$ alkyl, chloro, fluoro, bromo, hydroxy, benzoyloxy, $C_1$–$C_6$ alkoxy, $C_2$–$C_6$ acyloxy, amino, mono($C_1$–$C_6$) alkylamino, di($C_1$–$C_6$) alkylamino, morpholino, piperidino, 1-indolinyl, pyrrolidyl, trimethylsilyloxy or the group, —OCH(R$_7$)Z; V is $C_1$–$C_6$ alkyl or the unsubstituted, mono- or di-substituted aryl groups, phenyl or naphthyl; Y is hydrogen, hydroxy, $C_1$–$C_6$ alkyl, the unsubstituted, mono- or di-substituted aryl groups, phenyl or naphthyl, the group, —OCH($R_7$)Z, —O$R_8$, or —N($R_9$)($R_{10}$) or an unsubstituted, mono-substituted or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl; Z is —CN, —$CF_3$, chloro, fluoro, or —C(O)$R_{11}$; $R_7$ is hydrogen or $C_1$–$C_6$ alkyl; $R_{11}$ is hydrogen, $C_1$–$C_6$ alkyl or $C_1$–$C_6$ alkoxy; $R_8$ is hydrogen, $C_1$–$C_6$ alkyl, allyl, phenyl ($C_1$–$C_3$)alkyl, mono($C_1$–$C_6$)alkyl substituted phenyl ($C_1$–$C_3$)alkyl, mono($C_1$–$C_6$)alkoxy substituted phenyl($C_1$–$C_3$)alkyl, ($C_1$–$C_6$)alkoxy($C_2$–$C_4$)alkyl, $C_1$–$C_6$ haloalkyl, or the unsubstituted, mono- or di-substituted aryl groups, phenyl or naphthyl, said halo substituents being chloro or fluoro; and $R_9$ and $R_{10}$ are each selected from the group consisting of hydrogen, $C_1$–$C_6$ alkyl, $C_5$–$C_7$ cycloalkyl, phenyl, mono-substituted phenyl and di-substituted phenyl, each of said phenyl, naphthyl and heterocyclic ring substituents being $C_1$–$C_6$ alkyl or $C_1$–$C_6$ alkoxy;

(b) in the 6 position, a group $R_2$ selected from:
  (i) the group T or mono-T-substituted phenyl; or
  (ii) hydrogen, $C_1$–$C_6$ alkyl, $C_1$–$C_6$ alkoxy, the unsubstituted, mono- or di-substituted aryl groups, phenyl or naphthyl, amino, mono($C_1$–$C_6$)alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di-($C_1$–$C_6$) alkyl substituted diphenylamino, mono- or di-($C_1$–$C_6$)alkoxy substituted diphenylamino, morpholino, piperidino, dicyclohexylamino or pyrrolidyl, said aryl substituents being selected from the group consisting of $C_1$–$C_6$ alkyl, $C_1$–$C_6$ alkoxy, $C_3$–$C_6$ cycloalkyl, benzyl, amino, mono($C_1$–$C_6$)alkylamino, di($C_1$–$C_6$)alkylamino, dicyclohexylamino; diphenylamino, piperidino, morpholino, pyrrolidyl, pyridyl, bromo, chloro, fluoro, phenyl and naphthyl;

(c) in the 8 position, a group $R_3$ selected from the group consisting of:
  (i) the group, —O$R_{12}$, wherein $R_{12}$ is hydrogen, $C_1$–$C_6$ alkyl, the unsubstituted, mono- and di-substituted aryl groups, phenyl and naphthyl, phenyl($C_1$–$C_3$) alkyl, mono($C_1$–$C_6$)alkyl substituted phenyl($C_1$–$C_3$) alkyl, mono($C_1$–$C_6$)alkoxy substituted phenyl ($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, or $R_{12}$ is the group, —CH($R_{13}$)Q, wherein $R_{13}$ is hydrogen or $C_1$–$C_3$ alkyl and Q is —CN, —$CF_3$, or —COO$R_7$, $R_7$ being hydrogen or $C_1$–$C_6$ alkyl, each of said aryl group substituents being $C_1$–$C_6$ alkyl or $C_1$–$C_6$ alkoxy;
  (ii) the group, N($R_{14}$)$R_{15}$, wherein $R_{14}$ and $R_{15}$ are each selected from the group consisting of hydrogen, $C_1$–$C_8$ alkyl, phenyl, naphthyl, the heteroaromatic groups furanyl, benzofuran-2-yl, benzofuran-3-yl, thienyl, benzothien-2-yl, benzothien-3-yl, dibenzofuranyl, dibenzothienyl, benzopyridyl and fluorenyl, a $C_1$–$C_8$ alkylaryl group, $C_3$–$C_{20}$ cycloalkyl, $C_4$–$C_{20}$ bicycloalkyl, $C_5$–$C_{20}$ tricycloalkyl and $C_1$–$C_{20}$ alkoxyalkyl, wherein said aryl group is phenyl or naphthyl;
  (iii) a nitrogen containing ring represented by the following graphic formula:

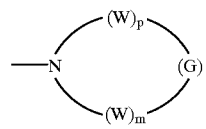

wherein W is selected from the group consisting of —$CH_2$—, —CH($R_{16}$)—, —C($R_{16}$)($R_{16}$)—, —CH(aryl)—, —C(aryl)$_2$—, —C($R_{16}$)(aryl)—, and G is selected from the group consisting of —W—, —O—, —S—, —S(O)—, —S($O_2$)—, —NH—, —N$R_{16}$—) and —N-aryl, wherein $R_{16}$ is $C_1$–$C_6$ alkyl, said aryl is phenyl or naphthyl, m is the integer 1, 2 or 3, and p is the integer 0, 1, 2 or 3 and when p is O, G is W; and (iv) a group represented by the following graphic formulae:

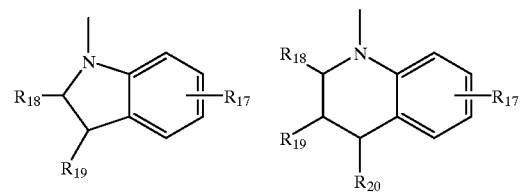

wherein $R_{17}$ is $C_1$–$C_6$ alkyl, $C_1$–$C_6$ alkoxy, fluoro or chloro, $R_{18}$, $R_{19}$ and $R_{20}$ are each hydrogen, $C_1$–$C_5$ alkyl, phenyl or naphthyl, or the groups $R_{18}$ and $R_{19}$ come together to form a ring of 5 to 8 carbon atoms including the ring carbon atoms; and (d) in the 9 position, a group $R_4$ being (c)(i) defined hereinbefore; or (e) $R_3$ and $R_4$ together form the following graphic formulae:

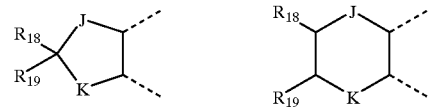

wherein J and K are each oxygen or the group —N$R_{14}$—; $R_{14}$, $R_{18}$ and $R_{19}$ being the same as defined hereinbefore; and (f) in the 2 position, B and B' are weak to moderate electron donor substituents; provided that said naphthopyran demonstrates a rating of at least 80 in the Relative ΔOD at Saturation Test.

2. The naphthopyran compound of claim 1 wherein,
(a) $R_1$ is the group T represented by the formula:

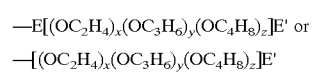

wherein —E— is —C(O)— or —$CH_2$—, E' is $C_1$–$C_3$ alkoxy or a polymerizable group, x, y and z are each a number between 0 and 50, and the sum of x, y and z is between 2 and 50; $R_2$ is the group T or mono-T-substituted phenyl; provided that if $R_1$ is not the group T or $R_2$ is not the group T or mono-T-substituted phenyl, then:

(b) $R_1$ is selected from the group consisting of —$CH_2$X, —C(V)$_2$X or —C(O)Y, wherein: X is hydrogen, $C_1$–$C_6$ alkyl, chloro, fluoro, bromo, hydroxy, benzoyloxy, $C_1$–$C_6$ alkoxy, $C_2$–$C_6$ acyloxy, amino, mono($C_1$–$C_6$) alkylamino, di($C_1$–$C_6$) alkylamino, morpholino, piperidino, 1-indolinyl, pyrrolidyl, trimethylsilyloxy or the group, —OCH($R_7$)Z; V is $C_1$–$C_6$ alkyl or the unsubstituted, mono- or di-substituted aryl groups, phenyl or naphthyl; Y is hydrogen, hydroxy, $C_1$–$C_6$ alkyl, the unsubstituted, mono- or di-substituted aryl groups, phenyl or naphthyl, the group, —OCH($R_7$)Z, —$OR_8$, or —N($R_9$)($R_{10}$) or an unsubstituted, mono-substituted or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl; Z is —CN, —$CF_3$, chloro, fluoro, or —C(O)$R_{11}$; $R_7$ is hydrogen or $C_1$–$C_6$ alkyl; $R_{11}$ is hydrogen, $C_1$–$C_6$ alkyl or $C_1$–$C_6$ alkoxy; $R_8$ is hydrogen, $C_1$–$C_6$ alkyl, allyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, ($C_1$–$C_6$)alkoxy($C_2$–$C_4$)alkyl, $C_1$–$C_6$ haloalkyl, or the unsubstituted, mono- or di-substituted aryl groups, phenyl or naphthyl, said halo substituent being chloro or fluoro; and $R_9$ and $R_{10}$ are each selected from the group consisting of hydrogen, $C_1$–$C_6$ alkyl, $C_5$–$C_7$ cycloalkyl, phenyl, mono-substituted phenyl and di-substituted phenyl, each of said phenyl, naphthyl and heterocyclic ring substituents being $C_1$–$C_6$ alkyl or $C_1$–$C_6$ alkoxy;

(c) $R_2$ is selected from hydrogen, $C_1$–$C_6$ alkyl, $C_1$–$C_6$ alkoxy, the unsubstituted, mono- or di-substituted aryl groups, phenyl or naphthyl, amino, mono($C_1$–$C_6$) alkylamino, di($C_1$–$C_6$)alkylamino, phenylamino, mono- or di-($C_1$–$C_6$)alkyl substituted phenylamino, mono- or di-($C_1$–$C_6$)alkoxy substituted phenylamino, diphenylamino, mono- or di-($C_1$–$C_6$)alkyl substituted diphenylamino, mono- or di-($C_1$–$C_6$)alkoxy substituted diphenylamino, morpholino, piperidino, dicyclohexylamino or pyrrolidyl, said aryl substituents being selected from the group consisting of $C_1$–$C_6$ alkyl, $C_1$–$C_6$ alkoxy, $C_3$–$C_6$ cycloalkyl, benzyl, amino, mono ($C_1$–$C_6$)alkylamino, di($C_1$–$C_6$)alkylamino, dicyclohexylamino, diphenylamino, piperidino, morpholino, pyrrolidyl, pyridyl, bromo, chloro, fluoro, phenyl and naphthyl;

(d) $R_3$ is selected from the group consisting of:
  (i) the group, —$OR_{12}$, wherein $R_{12}$ is hydrogen, $C_1$–$C_6$ alkyl, the unsubstituted, mono- and di-substituted aryl groups, phenyl and naphthyl, phenyl($C_1$–$C_3$) alkyl, mono($C_1$–$C_6$)alkyl substituted phenyl($C_1$–$C_3$) alkyl, mono($C_1$–$C_6$)alkoxy substituted phenyl ($C_1$–$C_3$)alkyl, $C_1$–$C_6$ alkoxy($C_2$–$C_4$)alkyl, $C_3$–$C_7$ cycloalkyl, mono($C_1$–$C_4$)alkyl substituted $C_3$–$C_7$ cycloalkyl, $C_1$–$C_6$ chloroalkyl, $C_1$–$C_6$ fluoroalkyl, allyl, or $R_{12}$ is the group, —CH($R_{13}$)Q, wherein $R_{13}$ is hydrogen or $C_1$–$C_3$ alkyl and Q is —CN, —$CF_3$, or —$COOR_7$, each of said aryl group substituents being $C_1$–$C_6$ alkyl or $C_1$–$C_6$ alkoxy;
  (ii) the group, —N($R_{14}$)$R_{15}$, wherein $R_{14}$ and $R_{15}$ are each selected from the group consisting of hydrogen, $C_1$–$C_8$ alkyl, phenyl, naphthyl, the heteroaromatic groups furanyl, benzofuran-2-yl, benzofuran-3-yl, thienyl, benzothien-2-yl, benzothien-3-yl, dibenzofuranyl, dibenzothienyl, benzopyridyl and fluorenyl, a $C_1$–$C_8$ alkylaryl group, $C_3$–$C_{20}$ cycloalkyl, $C_4$–$C_{20}$ bicycloalkyl, $C_5$–$C_{20}$ tricycloalkyl and $C_1$–$C_{20}$ alkoxyalkyl, wherein said aryl group is phenyl or naphthyl;

(iii) a nitrogen containing ring represented by the following graphic formula:

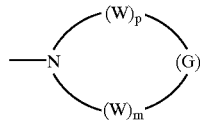

wherein W is selected from the group consisting of —$CH_2$—, —CH($R_{16}$)—, —C($R_{16}$)($R_{16}$)—, —CH (aryl)—, —C(aryl)$_2$—, —C($R_{16}$)(aryl)—, and G is selected from the group consisting of —W—, —O—, —S—, —S(O)—, —S($O_2$)—, —NH—, —$NR_{16}$— and —N-aryl, wherein $R_{16}$ is $C_1$–$C_6$ alkyl, said aryl is phenyl or naphthyl, m is the integer 1, 2 or 3, and p is the integer 0, 1, 2 or 3 and when p is O, G is W; and (iv) a group represented by the following graphic formulae:

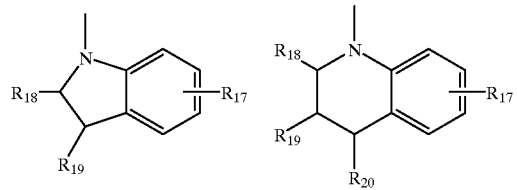

wherein $R_{18}$, $R_{19}$ and $R_{20}$ are each hydrogen, $C_1$–$C_5$ alkyl, phenyl or naphthyl, or the groups $R_{18}$ and $R_{19}$ come together to form a ring of 5 to 8 carbon atoms and $R_{17}$ is $C_1$–$C_6$ alkyl, $C_1$–$C_6$ alkoxy, fluoro or chloro;

(e) $R_4$ is the group (d)(i) defined hereinbefore; or
(f) $R_3$ and $R_4$ together form the following graphic formula:

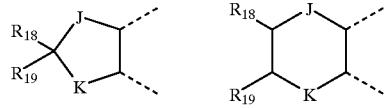

wherein J and K are each oxygen or the group —$NR_{14}$—;

(g) B and B' are each selected from the group consisting of:
  (i) mono-T-substituted phenyl;
  (ii) the unsubstituted, mono-, di-, and tri-substituted aryl groups, phenyl and naphthyl;
  (iii) 9-julolidinyl and the unsubstituted, mono-and di-substituted heteroaromatic groups pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl and fluorenyl, each of said aryl and heteroaromatic substituents in (g) (ii) and (iii) being selected from the group consisting of hydroxy, aryl, mono($C_1$–$C_6$) alkoxyaryl, di($C_1$–$C_6$)alkoxyaryl, mono($C_1$–$C_6$) alkylaryl, di($C_1$–$C_6$)alkylaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$) alkyl, aryl($C_1$–$C_6$)alkoxy, aryloxy, aryloxy($C_1$–$C_6$)

alkyl, aryloxy($C_1$–$C_6$)alkoxy, mono- and di-($C_1$–$C_6$) alkylaryl($C_1$–$C_6$)alkyl, mono- and di-($C_1$–$C_6$) alkoxyaryl($C_1$–$C_6$)alkyl, mono- and di-($C_1$–$C_6$) alkylaryl($C_1$–$C_6$)alkoxy, mono- and di-($C_1$–$C_6$) alkoxyaryl($C_1$–$C_6$)alkoxy, amino, mono($C_1$–$C_6$) alkylamino, di($C_1$–$C_6$)alkylamino, diarylamino, piperazino, N-($C_1$–$C_6$)alkylpiperazino, N-arylpiperazino, aziridino, indolino, piperidino, morpholino, thiomorpholino, tetrahydroquinolino, tetrahydroisoquinolino, pyrrolidyl, $C_1$–$C_6$ alkyl, $C_1$–$C_6$ chloroalkyl, $C_1$–$C_6$ fluoroalkyl, $C_1$–$C_6$ alkoxy, mono($C_1$–$C_6$)alkoxy($C_1$–$C_4$)alkyl, acryloxy, methacryloxy, bromo, chloro and fluoro, said aryl group being phenyl or naphthyl;
(iv) the unsubstituted or mono-substituted groups diarylamino, pyrazolyl, imidazolyl, indolyl, pyridyl, pyrazolinyl, imidazolinyl, pyrrolinyl, phenothiazinyl, phenoxazinyl, phenazinyl, acridinyl or carbazolyl, said aryl group being phenyl or naphthyl, each of said substituents being selected from the group consisting of $C_1$–$C_6$ alkyl, $C_1$–$C_4$ alkoxy, phenyl, fluoro, chloro and bromo;
(v) monosubstituted phenyl, having a substituent at the para position that is a linking group, —($CH_2$)t— or —O—($CH_2$)t—, wherein t is the integer 1, 2, 3, 4, 5 or 6, connected to an aryl group, which is a member of another photochromic naphthopyran;
(vi) the groups represented by the following graphic formulae:

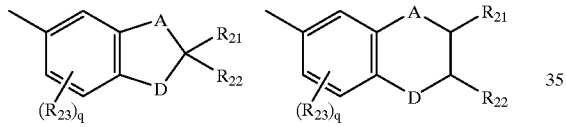

wherein A is methylene or oxygen and D is oxygen or substituted nitrogen, provided that when D is substituted nitrogen, A is methylene, said nitrogen substituents being selected from the group consisting of hydrogen, $C_1$–$C_6$ alkyl, and $C_2$–$C_6$ acyl; each $R_{23}$ is $C_1$–$C_6$ alkyl, $C_1$–$C_6$ alkoxy, hydroxy, chloro or fluoro; $R_{21}$ and $R_{22}$ are each hydrogen or $C_1$–$C_6$ alkyl; and q is the integer 0, 1, or 2;
(vii) $C_1$–$C_6$ alkyl, $C_1$–$C_6$ chloroalkyl, $C_1$–$C_6$ fluoroalkyl, $C_1$–$C_6$ alkoxy($C_1$–$C_4$)alkyl, $C_3$–$C_6$ cycloalkyl, mono($C_1$–$C_6$) alkoxy($C_3$–$C_6$)cycloalkyl, mono($C_1$–$C_6$)alkyl($C_3$–$C_6$)-cycloalkyl, chloro ($C_3$–$C_6$)cycloalkyl, fluoro($C_3$–$C_6$)cycloalkyl and $C_4$–$C_{12}$ bicycloalkyl; and
(viii) the group represented by the following graphic formula:

wherein L is hydrogen or $C_1$–$C_4$ alkyl and M is selected from the unsubstituted, mono-, and di-substituted members of the group consisting of naphthyl, phenyl, furanyl, and thienyl, each of said group substituents being $C_1$–$C_4$ alkyl, $C_1$–$C_4$ alkoxy, fluoro, and chloro; or (h) B and B' taken together form fluoren-9-ylidene, mono-, or di-substituted fluoren-9-ylidene or a member selected from the group consisting of saturated $C_3$–$C_{12}$ spiro-monocyclic hydrocarbon rings, saturated $C_7$–$C_{12}$ spiro-bicyclic hydrocarbon rings, and saturated $C_7$–$C_{12}$ spiro-tricyclic hydrocarbon rings, each of said fluoren-9-ylidene substituents being selected from the group consisting of $C_1$–$C_4$ alkyl, $C_1$–$C_4$ alkoxy, fluoro and chloro.
3. The naphthopyran of claim 2, wherein
(a) $R_1$ is selected from —$CH_2$X, —C(V)$_2$X or —C(O)Y, wherein: X is hydrogen, $C_1$–$C_4$ alkyl, hydroxy, benzoyloxy, $C_1$–$C_4$ alkoxy, $C_2$–$C_4$ acyloxy, amino, mono($C_1$–$C_4$)alkylamino, di($C_1$–$C_4$)alkylamino, morpholino, piperidino, 1-indolinyl, pyrrolidyl; V is $C_1$–$C_4$ alkyl or the unsubstituted, mono- or di-substituted aryl groups, phenyl or naphthyl; Y is hydrogen, hydroxy, $C_1$–$C_4$ alkyl, an unsubstituted, mono- or di-substituted phenyl, the group, —OCH($R_7$) Z, —O$R_8$, or —N($R_9$)($R_{10}$) or an unsubstituted or mono-substituted heterocyclic ring selected from the group consisting of 1-indolinyl, morpholino, piperidino, and 1-pyrrolidyl; Z is —CN or —C(O)$R_{11}$; $R_7$ is hydrogen or $C_1$–$C_4$ alkyl; $R_{11}$ is $C_1$–$C_4$ alkyl or $C_1$–$C_4$ alkoxy; $R_8$ is hydrogen, $C_1$–$C_4$ alkyl, phenyl ($C_1$–$C_2$)alkyl, mono($C_1$–$C_4$)alkyl substituted phenyl ($C_1$–$C_2$)alkyl, mono($C_1$–$C_4$)alkoxy substituted phenyl ($C_1$–$C_2$)alkyl, mono($C_1$–$C_4$)alkoxy($C_2$–$C_3$)alkyl, or an unsubstituted, mono- or di-substituted phenyl, said halo substituent being chloro or fluoro; and $R_9$ and $R_{10}$ are each selected from the group consisting of hydrogen, $C_1$–$C_4$ alkyl, $C_5$–$C_6$ cycloalkyl, phenyl, mono-substituted phenyl and di-substituted phenyl, each of said phenyl, naphthyl and heterocyclic ring substituents being $C_1$–$C_4$ alkyl or $C_1$–$C_4$ alkoxy;
(b) $R_2$ is selected from hydrogen, $C_1$–$C_4$ alkyl, $C_1$–$C_4$ alkoxy, the unsubstituted, mono- or di-substituted aryl groups, phenyl or naphthyl, amino, mono($C_1$–$C_4$) alkylamino, di($C_1$–$C_4$)alkylamino, morpholino, piperidino, or pyrrolidyl, said aryl substituents being selected from the group consisting of $C_1$–$C_4$ alkyl, $C_1$–$C_4$ alkoxy, $C_3$–$C_5$ cycloalkyl, benzyl, amino, mono ($C_1$–$C_4$)alkylamino, di($C_1$–$C_4$)alkylamino, piperidino, morpholino, chloro, fluoro and phenyl;
(c) $R_3$ is selected from the group consisting of;
(i) the group —O$R_{12}$, wherein $R_{12}$ is hydrogen, $C_1$–$C_4$ alkyl, the unsubstituted, mono- or di-substituted phenyl, phenyl($C_1$–$C_2$)alkyl, mono($C_1$–$C_4$)alkyl substituted phenyl($C_1$–$C_2$)alkyl, mono($C_1$–$C_4$) alkoxy substituted phenyl($C_1$–$C_2$)alkyl, $C_1$–$C_4$ alkoxy($C_2$–$C_3$)alkyl, $C_3$–$C_5$ cycloalkyl, mono ($C_1$–$C_4$)alkyl substituted $C_3$–$C_5$ cycloalkyl, $C_1$–$C_4$ chloroalkyl, $C_1$–$C_4$ fluoroalkyl or allyl, each of said phenyl substituents being $C_1$–$C_3$ alkyl or $C_1$–$C_3$ alkoxy; and
(ii) the group, —N($R_{14}$)$R_{15}$, wherein $R_{14}$ and $R_{15}$ are each selected from the group consisting of hydrogen, $C_1$–$C_4$ alkyl, phenyl, $C_1$–$C_6$ alkylphenyl, $C_3$–$C_{10}$ cycloalkyl and $C_1$–$C_{10}$ alkoxyalkyl; and
(iii) a nitrogen containing ring represented by the following graphic formula:

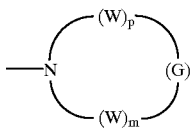

wherein W is selected from the group consisting of —CH$_2$—, —CH(R$_{16}$)—, —C(R$_{16}$)(R$_{16}$)—, —CH(aryl)—, —C(aryl)$_2$—, —C(R$_{16}$)(aryl)—, and G is selected from the group consisting of —W—, —O—, —NH—, —NR$_{16}$— and —N-aryl, wherein R$_{16}$ is C$_1$–C$_4$ alkyl, said aryl is phenyl or naphthyl, m is the integer 1, 2 or 3, p is the integer 0, 1, 2 or 3, and when p is O, G is W;

(d) R$_4$ is the group (c)(i) defined hereinbefore; or (e) R$_3$ and R$_4$ together form the following graphic formula:

wherein J and K are each oxygen or the group —NR$_{14}$—;

(f) B and B' are each selected from the group consisting of:
 (i) phenyl, mono-substituted phenyl, and di-substituted phenyl;
 (ii) the unsubstituted, mono-, and di-substituted aromatic heterocyclic groups furanyl, benzofuran-2-yl, thienyl, benzothien-2-yl and dibenzofuranyl, said phenyl and aromatic heterocyclic substituents in (f)(i) and (ii) being selected from the group consisting of hydroxy, amino, mono(C$_1$–C$_3$)alkylamino, di(C$_1$–C$_3$)alkylamino, piperidino, morpholino, C$_1$–C$_3$ alkyl, C$_1$–C$_3$ chloroalkyl, C$_1$–C$_3$ fluoroalkyl, C$_1$–C$_3$ alkoxy, mono(C$_1$–C$_3$)alkoxy(C$_1$–C$_3$)alkyl, fluoro and chloro;
 (iii) the groups represented by the following graphic formulae:

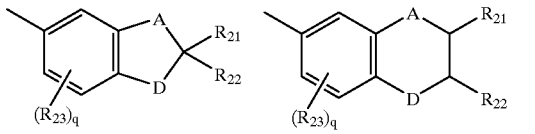

wherein A is methylene and D is oxygen, R$_{23}$ is C$_1$–C$_3$ alkyl or C$_1$–C$_3$ alkoxy, R$_{21}$ and R$_{22}$ are each hydrogen or C$_1$–C$_3$ alkyl; and q is the integer 0 or 1;
 (iv) C$_1$–C$_4$ alkyl; and
 (v) the group represented by the following graphic formula:

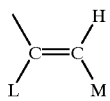

wherein L is hydrogen or methyl and M is phenyl or mono-substituted phenyl, said phenyl substituent being selected from the group consisting of C$_1$–C$_3$ alkyl, C$_1$–C$_3$ alkoxy, and fluoro; or (g) B and B' taken together form a fluoren-9-ylidene, mono-substituted fluoren-9-ylidene or a member selected from the group consisting of saturated C$_3$–C$_8$ spiro-monocyclic hydrocarbon rings, saturated C$_7$–C$_{10}$ spiro-bicyclic hydrocarbon rings, and saturated C$_7$–C$_{10}$ spiro-tricyclic hydrocarbon rings, each of said fluoren-9-xylidene substituents being selected from the group consisting of C$_1$–C$_3$ alkyl, C$_1$–C$_3$ alkoxy, fluoro and chloro.

4. The naphthopyran compound of claim 3 wherein, (a) R$_1$ is selected from —CH$_2$X, —C(V)$_2$X or —C(O)Y, wherein: X is hydrogen, C$_1$–C$_3$ alkyl, hydroxy, benzoyloxy, C$_1$–C$_3$ alkoxy, C$_2$–C$_3$ acyloxy, amino, mono(C$_1$–C$_3$)alkylamino, di(C$_1$–C$_3$)alkylamino, morpholino or piperidino; V is C$_1$–C$_3$ alkyl or an unsubstituted or mono-substituted phenyl; Y is hydrogen, hydroxy, C$_1$–C$_3$ alkyl, an unsubstituted or mono-substituted phenyl, the group, —OR$_8$, or —N(R$_9$)(R$_{10}$) or an unsubstituted or mono-substituted heterocyclic ring selected from the group consisting of 1-indolinyl, morpholino and piperidino; R$_8$ is hydrogen or C$_1$–C$_3$ alkyl; and R$_9$ and R$_{10}$ are each selected from the group consisting of hydrogen, C$_1$–C$_3$ alkyl, phenyl and mono-substituted phenyl each of said phenyl and heterocyclic ring substituents being C$_1$–C$_3$ alkyl or C$_1$–C$_3$ alkoxy;

(b) R$_2$ is hydrogen, C$_1$–C$_3$ alkoxy, C$_1$–C$_3$ alkyl or unsubstituted, mono- or di-substituted phenyl, said phenyl substituents being C$_1$–C$_3$ alkyl, C$_1$–C$_3$ alkoxy, chloro or fluoro;

(c) R$_3$ is selected from the group consisting of:
 (i) the group, —OR$_{12}$, wherein R$_{12}$ is hydrogen or C$_1$–C$_3$ alkyl;
 (ii) the group, —N(R$_{14}$)R$_{15}$, wherein R$_{14}$ and R$_{15}$ are each hydrogen or C$_1$–C$_3$ alkyl; and
 (iii) a nitrogen containing ring represented by the following graphic formula:

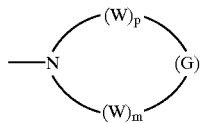

wherein W is —CH$_2$— and G is selected from the group consisting of —W— and —O—, m is the integer 1 or 2, p is the integer 0, 1 or 2, and when p is O, G is W;

(d) R$_4$ is the group (c)(i) defined hereinbefore; or (e) R$_3$ and R$_4$ together form the compound represented by the following graphic formula:

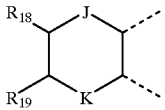

wherein J and K are each oxygen;

(f) B and B' are each selected from the group consisting of phenyl, mono-, and di-substituted phenyl, unsubstituted, mono-, and di-substituted aromatic heterocyclic groups furanyl, benzofuran-2-yl, thienyl, and benzothien-2-yl, each of said phenyl and aromatic heterocyclic substituents being selected from the group consisting of hydroxy, C$_1$–C$_3$ alkyl, C$_1$–C$_3$ alkoxy, fluoro and chloro and the group represented by the following graphic formula:

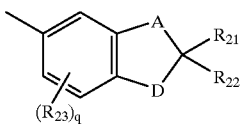

wherein A is methylene and D is oxygen, $R_{23}$ is $C_1$–$C_3$ alkyl or $C_1$–$C_3$ alkoxy, $R_{21}$ and $R_{22}$ are each hydrogen or $C_1$–$C_3$ alkyl, and q is the integer 0 or 1; or (g) B and B' taken together form fluoren-9-ylidene, adamantylidene, bornylidene, norbornylidene, or bicyclo(3.3.1)nonan-9-ylidene.

5. A naphthopyran compound selected from the group consisting of:
(a) 2,2-di(4-methoxyphenyl)-5-methoxycarbonyl-6-(3,4-dimethoxyphenyl)-8,9-dimethoxy-2H-naphtho[1,2-b]pyran;
(b) 2,2-diphenyl-5-methoxycarbonyl-6-(3,4-dimethoxyphenyl)-8,9-dimethoxy-2H-naphtho[1,2-b]pyran;
(c) 2,2-di (4-methoxyphenyl)-5-methoxycarbonyl-6-phenyl-8,9-dimethoxy-2H-naphtho[1,2-b]pyran;
(d) 2,2-di(4-methoxyphenyl)-5-methoxycarbonyl-6-phenyl-9,10-dihydro-2H-[1,4]dioxino[2',3':8,9]naphtho[1,2-b]pyran;
(e) 2,2-di (4-methoxyphenyl)-5-methoxycarbonyl-6-phenyl-8-morpholino-9-methoxy-2H-naphtho[1,2-b]pyran;
(f) 2-(4-methoxyphenyl)-2-phenyl-5-methoxycarbonyl-8,9-dimethoxy-2H-naphtho[1,2-b]pyran;
(g) 2, 2-diphenyl-5-methoxycarbonyl-8,9-dimethoxy-2H-naphtho[1,2-b]pyran;
(h) 2,2-di-(4-methoxyphenyl)-5-methoxycarbonyl-8,9-dimethoxy-2H-naphtho[1,2-b]pyran;
(i) 2,2-di(4-methoxyphenyl)-5-methoxycarbonyl-6-phenyl-8-piperidino-9-methoxy-2H-naphtho[1,2-b]pyran;
(j) 2,2-di(4-methoxyphenyl)-5-methoxycarbonyl-6-methyl-8,9-dimethoxy-2H-naphtho[1,2-b]pyran; and
(k) 2,2-diphenyl-5-methoxycarbonyl-6-phenyl-2H-[1,3]dioxolo[4',5':8,9]naphtho[1,2-b]pyran.

6. A photochromic article comprising a polymeric organic host material and a photochromic amount of the naphthopyran compound of claim 1.

7. The photochromic article of claim 6 wherein the polymeric organic host material is selected from the group consisting of poly($C_{1-12}$)alkyl methacrylates), poly(oxyalkylene) dimethacrylates, poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, polythiourethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol methacrylate monomers, alkoxylated polyhydric alcohol acrylate monomers and diallylidene pentaerythritol monomers.

8. The photochromic article of claim 7 wherein the polymeric organic host material is a solid transparent polymer selected from the group consisting of poly(methyl methacrylate), poly(ethylene glycol) bismethacrylate, poly (ethoxylated bisphenol A) dimethacrylate, thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers.

9. The photochromic article of claim 8 wherein the photochromic compound is present in an amount of from about 0.05 to 2.0 milligram per square centimeter of organic host material surface to which the photochromic substance (s) is incorporated or applied.

10. The photochromic article of claim 9 wherein the article is a lens.

11. A photochromic article comprising a polymeric organic host material selected from the group consisting of poly(methyl methacrylate), poly(ethylene glycol) bismethacrylate, poly(ethoxylated bisphenol A) dimethacrylate, thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers and a photochromic amount of the naphthopyran compound of claim 2.

12. A photochromic article comprising a polymeric organic host material selected from the group consisting of poly(methyl methacrylate), poly(ethylene glycol) bismethacrylate, poly(ethoxylated bisphenol A) dimethacrylate, thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of the naphthopyran compound of claim 4.

13. A photochromic article comprising a polymerizate of an optical organic resin monomer and a photochromic amount of the naphthopyran compound of claim 1.

14. The photochromic article of claim 13 wherein the refractive index of the polymerizate is from about 1.48 to about 1.75.

15. The photochromic article of claim 13 wherein the polymerizate is an optical element.

16. The photochromic article of claim 15 wherein the optical element is an ophthalmic lens or a contact lens.

17. A photochromic article comprising, in combination, a solid transparent polymeric organic host material, and a photochromic amount of each of (a) at least one naphthopyran compound of claim 1, and (b) at least one other organic photochromic compound having at least one activated absorption maxima within the range of between about 400 and 700 nanometers.

18. The photochromic article of claim 17 wherein the polymeric organic host material is a solid transparent homopolymer or copolymer selected from the group consisting of poly(methyl methacrylate), poly(ethylene glycol) bismethacrylate, poly(ethoxylated bisphenol A) dimethacrylate, thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers.

19. The photochromic article of claim 17 wherein the organic photochromic compound (b) is selected from the group consisting of naphthopyrans, benzopyrans, phenanthropyrans, indenonaphthopyrans, oxazine, metaldithiozonates, fulgides, fulgimides, and mixtures of such photochromic compounds.

20. The photochromic article of claim 19 wherein the photochromic compound is present in an amount of from about 0.05 to 2.0 milligram per square centimeter of organic host material surface to which the photochromic substance (s) is incorporated or applied.

21. The photochromic article of claim 20 wherein the article is an ophthalmic lens or a contact lens.

22. A photochromic article comprising, in combination, a polymeric organic host material selected from the group consisting of poly(methyl methacrylate), poly(ethylene glycol) bismethacrylate, poly(ethoxylated bisphenol A) dimethacrylate, thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one naphthopyran compound of claim 2, and (b) at least one other organic photochromic compound having at least one activated absorption maxima within the range of between about 400 and 700 nanometers.

23. A photochromic article comprising, in combination, a polymeric organic host material selected from the group consisting of poly(methyl methacrylate), poly(ethylene glycol) bismethacrylate, poly(ethoxylated bisphenol A) dimethacrylate, thermoplastic polycarbonate, poly(vinyl acetate), polyvinylbutyral, polyurethane, polythiourethane and polymers of members of the group consisting of diethylene glycol bis(allyl carbonate) monomers, diethylene glycol dimethacrylate monomers, ethoxylated phenol methacrylate monomers, diisopropenyl benzene monomers and ethoxylated trimethylol propane triacrylate monomers, and a photochromic amount of each of (a) at least one naphthopyran compound of claim 4, and (b) at least one other organic photochromic compound having at least one activated absorption maxima within the range of between about 400 and 700 nanometers.

* * * * *

UNITED STATES PATENT AND TRADEMARK OFFICE
CERTIFICATE OF CORRECTION

PATENT NO. : 6,348,604 B1
DATED : February 19, 2002
INVENTOR(S) : Nelson et al.

Page 1 of 1

It is certified that error appears in the above-identified patent and that said Letters Patent is hereby corrected as shown below:

Column 30,
Line 51, "–E[$(OC_2H_4)_x(OC_3H_6)_y(OC_4H_6)_z$E'" should be
-- –E[$(OC_2H_4)_x(OC_3H_6)_y(OC_4H_8)_z$E' --.

Column 32,
Line 12, please remove the ")" at the end of the line.

Signed and Sealed this

Tenth Day of September, 2002

Attest:

Attesting Officer

JAMES E. ROGAN
Director of the United States Patent and Trademark Office